United States Patent
Hinds et al.

(10) Patent No.: US 11,072,830 B2
(45) Date of Patent: Jul. 27, 2021

(54) METHODS FOR BREAST CANCER RISK ASSESSMENT

(71) Applicant: Genetic Technologies Limited, Fitzroy (AU)

(72) Inventors: David A. Hinds, Sunnyvale, CA (US); Bryan Walser, Menlo Park, CA (US)

(73) Assignee: GENETIC TECHNOLOGIES LIMITED, Fizroy (AU)

( * ) Notice: Subject to any disclaimer, the term of this patent is extended or adjusted under 35 U.S.C. 154(b) by 0 days.

(21) Appl. No.: 15/814,255

(22) Filed: Nov. 15, 2017

(65) Prior Publication Data

US 2018/0080089 A1 Mar. 22, 2018

Related U.S. Application Data

(63) Continuation of application No. 12/920,815, filed as application No. PCT/AU2010/000675 on Jun. 1, 2010, now abandoned.

(60) Provisional application No. 61/258,420, filed on Nov. 5, 2009, provisional application No. 61/182,809, filed on Jun. 1, 2009.

(51) Int. Cl.
C12Q 1/6886 (2018.01)

(52) U.S. Cl.
CPC ..... *C12Q 1/6886* (2013.01); *C12Q 2600/106* (2013.01); *C12Q 2600/112* (2013.01); *C12Q 2600/156* (2013.01); *C12Q 2600/172* (2013.01)

(58) Field of Classification Search
None
See application file for complete search history.

(56) References Cited

U.S. PATENT DOCUMENTS

| | | | |
|---|---|---|---|
| 6,812,339 B1 | 11/2004 | Venter | |
| 7,127,355 B2 | 10/2006 | Cox et al. | |
| 7,529,685 B2 | 5/2009 | Davies et al. | |
| 9,051,617 B2 | 6/2015 | Cox | |
| 2002/0123095 A1* | 9/2002 | Kalush | C07K 14/70567 435/69.1 |
| 2003/0092019 A1 | 5/2003 | Meyer | |
| 2003/0099964 A1 | 5/2003 | Patil | |
| 2003/0108910 A1 | 6/2003 | Toland | |
| 2003/0157488 A1 | 8/2003 | Cox | |
| 2004/0002071 A1 | 1/2004 | Ralph | |
| 2004/0023237 A1 | 2/2004 | Patil | |
| 2004/0191783 A1* | 9/2004 | Leclercq | C12Q 1/6837 506/16 |
| 2004/0210400 A1 | 10/2004 | Konvicka | |
| 2004/0229224 A1 | 11/2004 | Frazer | |
| 2004/0241657 A1 | 12/2004 | Patil | |
| 2005/0003410 A1 | 1/2005 | Frazer | |
| 2005/0019787 A1 | 1/2005 | Berno | |
| 2005/0084849 A1 | 4/2005 | Moskowitz | |
| 2005/0196770 A1 | 9/2005 | Cox | |
| 2007/0037198 A1 | 2/2007 | Cox et al. | |
| 2007/0166738 A1 | 7/2007 | Cox et al. | |
| 2008/0131887 A1 | 6/2008 | Stephan et al. | |
| 2009/0087854 A1 | 4/2009 | Cox et al. | |
| 2009/0208962 A1 | 8/2009 | Cox et al. | |
| 2009/0239226 A1 | 9/2009 | Cox et al. | |
| 2009/0239763 A1 | 9/2009 | Cox et al. | |
| 2011/0015081 A1* | 1/2011 | Stacey | C12Q 1/6886 506/7 |
| 2011/0015092 A1 | 1/2011 | Cox et al. | |
| 2011/0200588 A1 | 8/2011 | Cox et al. | |
| 2011/0294681 A1 | 12/2011 | Hinds et al. | |
| 2016/0222469 A1 | 8/2016 | Allman | |
| 2017/0275707 A1 | 9/2017 | Cox | |
| 2018/0305764 A1 | 10/2018 | Allman | |

FOREIGN PATENT DOCUMENTS

| | | |
|---|---|---|
| WO | WO 95/011995 | 5/1995 |
| WO | WO 98/020167 | 5/1998 |
| WO | WO 2003/025141 | 3/2003 |
| WO | WO 2005/014846 | 2/2005 |
| WO | WO 2005/024067 | 3/2005 |
| WO | WO 00/33161 | 6/2005 |
| WO | WO 2005/086770 | 9/2005 |
| WO | 2007/064776 | 6/2007 |
| WO | WO 2007/150044 | 12/2007 |
| WO | 2008/117314 | 10/2008 |
| WO | 2008/146309 | 12/2008 |
| WO | WO 2009/009752 | 1/2009 |
| WO | WO 2009/097270 | 8/2009 |
| WO | WO 2010/017520 | 2/2010 |
| WO | WO 2010/030929 | 3/2010 |
| WO | WO 2010/139006 | 9/2010 |
| WO | WO 2013/151413 | 10/2013 |

OTHER PUBLICATIONS

Lee et al. (Cancer Epidemiol Biomarkers Prve Jan. 2008 vol. 17 p. 258) (Year: 2008).*
Gail et al. (JNCI 2008 VO. 100 p. 1037) (Year: 2008).*
Millikan et al. (Cancer Epidemiology, Biomarkers and Prevention 2005 vol. 14 p. 2326) (Year: 2005).*
Mcinerney et al. (Breast Cancer Res Treat Nov. 13, 2008 vol. 117 p. 151) (Year: 2008).*
Jun. 11, 2012 Office Action dated in connection with U.S. Appl. No. 12/920,815.
Jul. 11, 2012 Response filed in connection with U.S. Appl. No. 12/920,815.

(Continued)

*Primary Examiner* — Katherine D Salmon

(74) *Attorney, Agent, or Firm* — Gary J. Gershik

(57) ABSTRACT

The present invention relates to methods and systems for assessing the overall risk of a human female subject for developing a breast cancer phenotype. In particular, the present invention relates to combining clinical risk assessment and genetic risk assessment to improve risk analysis.

20 Claims, 2 Drawing Sheets

Specification includes a Sequence Listing.

(56) References Cited

OTHER PUBLICATIONS

Sep. 21, 2012 Office Action issued in connection with U.S. Appl. No. 12/920,815.
Feb. 21, 2013 Response filed in connection with U.S. Appl. No. 12/920,815.
Jun. 24, 2013 Office Action issued in connection with U.S. Appl. No. 12/920,815.
Dec. 23, 2013 Response filed in connection with U.S. Appl. No. 12/920,815.
Apr. 20, 2015 Office Action issued in connection with U.S. Appl. No. 12/920,815.
Oct. 20, 2015 Response filed in connection with U.S. Appl. No. 12/920,815.
Jun. 14, 2016 Office Action issued in connection with U.S. Appl. No. 12/920,815.
Dec. 14, 2016 Response filed in connection with U.S. Appl. No. 12/920,815.
Jun. 19, 2017 Office Action issued in connection with U.S. Appl. No. 12/920,815.
Extended European Search Report, dated Oct. 18, 2012 in connection with European Patent Application No. 10782820.4.
European Search Opinion, dated Oct. 18, 2012 in connection with European Patent Application No. 10782820.4.
Patent Examination Report No. 1, dated Oct. 9, 2012 in connection with Australian Patent Application No. 2010256343.
Anonymous, "Perlegen Builds Commercial Group to Support Upcoming MammaPLUS(™) Launch" Evaluatepharma Press Release, Apr. 28, 2009.
Anonymous, "Perlegen Introduces BRAVAGen™ Breast Cancer Risk Stratification Test" Medical News Today, Sep. 24, 2009.
Bondy et al. (1994) "Validation of a Breast Cancer Risk Assessment Model in Women With a Positive Family History" Journal of the National Cancer Institute, vol. 86, No. 8, pp. 620-625.
Costantino et al. (1999) "Validation Studies for Models Projecting the Risk of Invasive and Total Breast Cancer Incidence" Journal of the National Cancer Institute, vol. 91, No. 18, pp. 1541-1548.
Jupe et al. (2007) "The OncoVue (R) model for predicting breast cancer risk" Breast Cancer Research and Treatment vol. 106 No. Suppl. 1, p. S179.
Matsuno et al. (2011) "Projecting Individualized Absolute Invasive Breast Cancer Risk in Asian and Pacific Islander American Women" J Natl Cancer Inst 2011;13:951-961.
Schonfeld et al. (2010) "Effect of Changing Breast Cancer Incidence Rates on the Calibration of the Gail Model" J Clin Oncol 28, pp. 1-8.
Spiegelman et al. (1994) "Validation of the Gail et al. Model for Predicting Individual Breast Cancer Risk" Journal of the National Cancer Institute 68(8):600-607.
Zheng et al. (2010) "Genetic and Clinical Predictors for Breast Cancer Risk Assessment and Stratification Among Chinese Women" Journal of the National Cancer Institute 102(13):972-981.
Liu et al. (2006) "The role of Self-Defined Race/Ethnicity in Population Structure Control" Annals of Human Genetics 70:496-505.
Merriam-Webster Dictionary definition for "Caucasian," available from www.merriam-webster.com/medical/Caucasian, accessed Nov. 2, 2012.
Nov. 25, 2013 Office Action, issued in connection with U.S. U.S. Appl. No. 12/370,972.
Breast Cancer. American Cancer Society. 2013, pp. 1-134. Downloaded from Cancer.org on Oct. 17, 2013.
Rodi et al, (2003) "A Strategy for the Rapid Discovery of Disease Markers Using the MassARRAYTM System." BioTechniques, 32:S62-S69.
Db SNP ss No. 23605537 (www.ncbi.nlm.nih.gov/projects/SNP/snp_ss.cgi?subsnp_id=23605537) Aug. 20, 2004.
Db SNP ss No. 23575498 (www.ncbi.nlm.nih.gov/SNP/snp_ss.cgi?subsnp_id=23575498) Aug. 20, 2004.
Db SNP ss No. 24561224 (www.ncbi.nlm.nih.gov/projects/SNP/snp_ref.cgi?rs=rs3817198) Aug. 20, 2004.

Armstrong et al. (2000) "Assessing the Risk of Breast Cancer. The New England Journal of Medicine," 342(8):564-571.
Jul. 9, 2013 Response filed in connection with U.S. Appl. No. 12/890,272.
Jul. 10, 2013 Interview Summary issued in connection with U.S. Appl. No. 12/890,272.
Advani and Morena-Aspitia (2014) Breast Cancer: Targets & Therapy; 6: 59-71.
American Cancer Society: (2013) Breast Cancer Facts & Figures 2013-2014. Atlanta (GA), American Cancer Society Inc, 12.
Brentall et al. (2014) British Journal of Cancer 110: 827-828.
Chen et al. (2004) Stat Appl Genet Mol Biol. 3: Article 21.
Claus et al. (1991) Am J Hum Genet. 48: 232-242.
Claus et al. (1993) Breast Cancer Res Treat. 28: 115-120.
Cuzick et al. (2014) Journal of Clinical Oncology 43:Abstract No. 1519.
Darabi et al. (2012) Breast Cancer Research 14: R25.
De la Cruz (2014) Prim Care Clin Office Pract; 41: 283-306.
Dite et al. (2013) Breast Cancer Res Treat. 139: 887-896.
Ellis et al. (2006) Genetic Epidemiology 30: 48-61.
(1997a) FASEB Journal 11:A879.
Fodor (1997b) Science 277: 393-395.
Garcia (2004) Pediatrics 113:1394.
Ho et al. (2013) The Malaysian Journal of Pathology 1: 33-43.
Mackarem et al. (2001) The Breast Journal 2001 vol. 7 p. 34.
Mahoney et al. (2008) Cancer J Clin; 58: 347-371.
Mazzola et al. (2014) Cancer Epidemiol Biomarkers Prev. 23: 1689-1695.
McCarthy et al. (2013) Breast Cancer Research & Treatment 138: 889-898.
Parmigiani et al. (1998) Am J Hum Genet. 62: 145-158.
Parmigiani et al. (2007) Ann Intern Med. 1479: 441-450.
Raskin et al. (2008) Cancer Epidemiol Biomarkers Prey Vo. 17 p. 1060.
Ruiz-Narvaez (2010) Breast Cancer Res Treat vol. 123 p. 525.
Saslow et al. (2007) CA Cancer J Clin. 57: 75-89.
Schwartz (2001) N. Engl. J. Med. 344(18):1392-1393.
Sorlie et al. (2001) Proc. Natl. Acad. Sci., 98: 10869-10874.
Visvanathan et al. (2009) Journal of Clinical Oncology. 27: 3235-3258.
WIRES: Questions and Answers. "Average risk of breast cancer and general information".
International Preliminary Report on Patentability, dated Dec. 6, 2011, in connection with PCT International Application No. PCT/AU2010/000675.
International Search Report, dated Aug. 13, 2010 in connection with PCT International Application No. PCT/AU2010/000675.
"Perlegen Builds Commercial Group to Support Upcoming MammaPLUS(™) Launch", <URL http://www.evaluatepharma.com/Universal/View.aspx?type=Story&id =184247> published on Apr. 28, 2009.
"Perlegen Introduces BREVAGen Breast Cancer Risk Stratification test" <http://www.medicalnewstoday.com/releases/165123.php> retrieved by the International Search Authority on Jun. 23, 2010 in connection with PCT International Application No. PCT/AU2010/000675.
Easton et al., "Genome-wide association study identifies novel breast cancer susceptibility loci" Nature (2007) 447(7148):1087-1093.
Ahmed et al., "Newly discovered breast cancer susceptibility loci on 3p24 and 17q23.2" Nature Genetics (2009) 41(5):585-590.
Antoniou et al. "A comprehensive model for familial breast cancer incorporating BRCA1, BRCA2 and other genes" British Journal of Cancer (2002) 86, 76-83.
Antoniou et al., "The BOADICEA model of genetic susceptibility to breast and ovarian cancer" British Journal of Cancer (2004) 91, 1580-1590.
Antoniou et al., "Common variants in LSP1, 2q25 and 8q24 and breast cancer risk for BRCA1 and BRCA2 mutation carriers" Human Genetics (2009) 18(22):4442-4456.
Barringer et al., "Blunt-end and single-strand ligations by *Escheria coli* ligase: influence on and in vitro amplification scheme" Gene (1990) 89, 117-122.

(56) References Cited

OTHER PUBLICATIONS

Beaucage and Caruthers, "Deoxynucleoside Phosphoramidites—A New Class of Key Intermediates for Deoxypolynucleotide Synthesis" Tetrahedron Letters (1981) 22(20):1859-1862.
Blok and Kramer, "Amplifiable hybridization proves containing a molecular switch" Molecular and Cellular Probes (1997) 11, 187-194.
Bonnet et al., "Thermodynamic basis of the enhanced specificity of structured DNA probes" PNA (1999) 96:6171-6176.
Chee et al., "Accessing genetic information with high-density DNA arrays" Science 274,n5287 (1996):610+. Expanded Academic ASAP. Web. Oct. 18, 2010. pp. 1-8.
Cheng et al., "Long PCR" Product Review, Nature (1994) 369:684-685.
Chlebowski et al., "Predicting Risk of Breast Cancer in Postmenopausal Women by Hormone Receptor Status" J Natl Cancer Inst (2007) 99:1695-1705.
Claus et al., "Autosomal Dominant Inheritance of Early-Onset Breast Cancer" Cancer (1994) 73(3):643-651.
Claus et al., "Effect of BRCA1 and BRCA2 on the Association Between Breast Cancer Risk and Family History" Journal of the National Cancer Institute (1998) 90(23):1824-1829.
Cook et al., "The Effect of Including C-Reactive Protein in Cardiovascular Risk Prediction Models for Women" Annals of Internal Medicine (2006) 145:21-29.
Costantino et al., "Validation Studies for Models Projecting the Risk of Invasive and Total Breast Cancer Incidence" J Natl Cancer Inst (1999) 91:1541-8.
Devlin and Risch, "A Comparison of Linkage Disequilibrium Measures for Fine-Scale Mapping" Genomics (1995) 29:311-322.
Evans et al., "A new scoring system for the chances of identifying a BRCA1/2 mutation outperforms existing models including BRCAPRO" J Med Genet (2004) 41:474-480.
Fang et al., "Designing a Novel Molecular Beacon for Surface-Immobilized DNA Hybridization Studies" J Am Chem Soc (1999).
Fodor, "Massively parallel genomics" Science 277.5324 (1997): 393+ Expanded Academic ASAP. Web. Sep. 28, 2010, pp. 1-3.
Gail et al., "Projecting Individualized Probabilities of Developing Breast Cancer for White Females Who are Being Examined Annually" J Natl Cancer Inst (1989) 81:1879-1886.
Gail et al., "Weighing the Risks and Benefits of Tamoxifen Treatment for Preventing Breast Cancer" J Natl Cancer Inst (1999) 91:1829-46.
Gail et al., "Projecting Individualized Absolute Invasive Breast Cancer Risk in African American Women" J Natl Cancer Inst (2007) 99:1782-92.
Gail, "Discriminatory Accuracy From Single-Nucleotide Polymorphisms in Models to Predict Breast Cancer Risk" J Natl Cancer Inst (2008) 100:1037-1041.
Gail, "Value of Adding Single-Nucleotide Polymorphism Genotypes to a Breast Cancer Risk Model" J Natl Cancer Inst (2009) 101:959-963.
Gold et al., "Genome-wide association study provides evidence for a breast cancer risk locus at 6q22.33" PNAS (2008) 105(11):4340-4345.
Guatelli et al., "Isothermal, in vitro amplification of nucleic acids by a multienzyme reaction modeled after retroviral replication" PNAS (1990) 87:1874-1878.
Hsuih et al., "Novel, Ligation-Dependent PCT Assay for Detection of Hepatitis C Virus in Serum" Journal of Clinical Microbiology (1996) 34(3):501-507.
Jonker et al., "Modeling Familial Clustered Breast Cancer Using Published Data" Cancer Epidemiology, Biomarkers & Prevention (2003) 12:1479-1485.
Kelemen et al., "Genetic Variation in the Chromosome 17q23 Amplicon and Breast Cancer Risk" Cancer Epidemiol Biomarkers Prey (2009) 18(6):1864-8.
Kostrikis, "Spectral genotyping of human alleles" Science 279.5354 (1998): 1228+. Expanded Academic ASAP. Web. Oct. 18, 2010, pp. 1-4.
Kwoh et al., "Transcription-based amplification system and detection of amplified human immunodeficiency virus type 1 with a bead-based sandwich hybridization format" PNAS (1989).
Landegren et al., "A ligase-mediated gene detection technique" Science 241.4869 (1998): 1077+. Expanded Academic ASAP. Web. Sep. 28, 2010 pp. 1-2.
Leone et al., "Molecular beacon probes combined with amplification by NASBA enable homogeneous, real-time detection of RNA" Nucleic Acids Research 26(9):2150-2155.
Lockhart, "Mutant yeast on Drugs" Nature Medicine (1998) 4(11):1235-1236.
Marras et al., "Multiplex detection of single-nucleotide variations using molecular beacons" Genetic Analysis: Biomolecular Engineering (1999) 14:151-156.
Mealiffe et al., "Assessment of Clinical Validity of a Breast Cancer Risk Model Combining Genetic and Clinical Information" J Natl Cancer Inst (2010) 102:1618-1627.
Needham-VanDevanter et al., "Characterization of an adduct between CC-1065 and a defined oligodeoxynucleotide duplex" Nucleic Acids Research (1984) 12(15): 6159-6168.
Pencina et al., "Evaluating the added predictive ability of a new marker: From area under the ROC curve to reclassification and beyond" Statistics in Medicine (2008) 27:157-172.
Pepe and Janes, "Gauging the Performance if SNPs, Biomarkers, and Clinical Factors for Ptedicting Risk of Breast Cancer" J Natl Cancer Inst (2008) 100(14):978-979.
Peto and Mack, "High constant incidence in twins and other relatives of women with breast cancer" Nature Genetics (2000) 26:411-414.
Pharoah et al., "Polygenes, Risk Prediction, and Targeted Prevention of Breast Cancer" N Eng J Med (2008) 358:2796-803.
Rockhill et al., "Validation of the Gail et al. Model of Breast Cancer Risk Prediction and Implications for Chemoprevention" J Natl Cancer Inst (2001) 93:358-66.
Sapolsky et al., "High-throughput polymorphism screening and genotyping with high-density oligonucleotide arrays" Genetic Analysis: Biomolecular Engineering (1999) 14:187-192.
Service et al., "Microchip Arrays Put DNA on the Spot" Science 282.53388 (1998): 396. Expanded Academic ASAP. Web. Sep. 23, 2010. pp. 1-3.
Service et al., "Coming Soon: The Pocket DNA Sequencer" Science 282.5388 (1998): 399. Expanded Academic ASAP. Web. Sep. 28, 2010 pp. 1-3.
Slatkin and Excoffier, "Testing for linkage disequilibrium in genotypic data using the Expectation-Maximization algorithm" Heredity (1996) 76, 377-383.
Sokol et al., "Real time detection of DNA-RNA hybridization in living cells" PNAS (1998) 95:11538-11543.
Sooknanan and Malek, "NASBA A detection and amplification system uniquely suited for RNA" Biotechnology (1995) 13:563-564.
Stacey et al., "Common variants on chromosomes 2q35 and 16q12 confer susceptibility to estrogen receptor-positive breast cancer" Nature Genetics (2007) 39(7):865-869.
Stacey et al., "Common variants on chromosome 5p12 confer susceptibility to estrogen receptor-positive breast cancer" Nature Genetics (2008) 40(6):703-706.
Thomas et al., "A multistage genome-wide association study in breast cancer identifies two new risk alleles at 1p11.2 and 14q24.1 (RAD51L1)" Nature Genetics (2009) 41(4):579-584.
Turnbull et al., "Genome-wide association study identifies five new breast cancer susceptibility loci" Nature Genetics (2010) 42.(6):504-507 and Online Methods.
Tyagi and Kramer, "Molecular Beacons: Probes that Fluoresce upon Hybridization" Nature Biotechnology (1996) 14:303-308.
Tyagi et al., "Multicolor molecular beacons for allele discrimination" Nature Biotechnology (1998) 16:49-53.
Tyrer et al., "A breast cancer prediction model incorporating familial and personal risk factors" Statistics in Medicine (2004) 23:1111-1130.
Van Asperen et al., "Risk Estimation for Healthy Women from Breast Cancer Families: New Insights and New Strategies" Cancer Epidemiology, Biomarkers & Prevention (2004) 13, 87-93.

(56) References Cited

OTHER PUBLICATIONS

Van Brunt, "Amplifying Genes: PCT and its Alternatives" Bio/Technology (1990) 8, pp. 291, 292 and 294.
Vet et al., "Multiplex detection of four pathogenic retroviruses using molecular beacons" PNAS (1999) 96: 6394-6399.
Wu and Wallace, "The Ligation Amplification Reaction (LAR)—Amplification of Specific DNA Sequences Using Sequential Rounds of Template-Dependent Ligation" Genomics (1989) 4, 560-569.
Zhang et al., "Automated and Integrated System for High-Throughput DNA Genotyping Directly from Blood" Anal Chem (1999) 71, 1138-1145.
"Breast cancer breakthrough", <URL http://au.news.yahoo.com/today-tonight/health/article/-/13691294/breast-cancer-breakthrough> published on May 15, 2012.
U.S. Appl. No. 10/970,761, filed Oct. 20, 2004, Frazer.
U.S. Appl. No. 60/566,302, filed Apr. 28, 2004, Cox.
U.S. Appl. No. 60/590,534, filed Jul. 22, 2004, Cox.
May 5, 2011 Office Action issued in connection with U.S. Appl. No. 12/890,272 (Exhibit 1).
Jun. 3, 2011 Response filed in connection with U.S. Appl. No. 12/890,272 (Exhibit 2).
Jul. 8, 2011 Response, filed in connection with U.S. Appl. No. 12/890,272 (Exhibit 3).
Sep. 29, 2011 Office Action issued in connection with U.S. Appl. No. 12/890,272 (Exhibit 4).
Mar. 29, 2012 Response filed in connection with U.S. Appl. No. 12/890,272 (Exhibit 5).
Apr. 2, 2012 Applicant-Initiated Interview Summary issued in connection with U.S. Appl. No. 12/890,272 (Exhibit 6).
Apr. 23, 2012 Office Action issued in connection with U.S. Appl. No. 12/890,272 (Exhibit 7).
May 24, 2012 Response filed in connection with U.S. Appl. No. 12/890,272 (Exhibit 8).
May 24, 2012 Applicant-Initiated Interview Summary issued in connection with U.S. Appl. No. 12/890,272 (Exhibit 9).
Jun. 1, 2012 Response filed in connection with U.S. Appl. No. 12/890,272 (Exhibit 10).
Jun. 26, 2012 Response filed in connection with U.S. Appl. No. 12/890,272 (Exhibit 11).
Aug. 23, 2012 Office Action issued in connection with U.S. Appl. No. 12/890,272 (Exhibit 12).
Nov. 16, 2012 Applicant-Initiated Interview Summary, including attached Oct. 26, 2012 facsimile, issued in connection with U.S. Appl. No. 12/890,272 (Exhibit 13).
Nov. 21, 2012 Response filed in connection with U.S. Appl. No. 12/890,272 (Exhibit 14).
Jan. 9, 2013 Office Action issued in connection with U.S. Appl. No. 12/890,272 (Exhibit 15).
Feb. 13, 2013 Applicant-Initiated Interview Summary issued in connection with U.S. Appl. No. 12/890,272 (Exhibit 16).
Mar. 8, 2013 Response filed in connection with U.S. Appl. No. 12/890,272 (Exhibit 17).
Mar. 5, 2013 Applicant-Initiated Interview Summary, including attached Proposed Amendments to the Claims, issued in connection with U.S. Appl. No. 12/890,272 (Exhibit 18).
Jun. 20, 2013 Advisory Action issued in connection with U.S. Appl. No. 12/890,272 (Exhibit 19).
Dec. 18, 2013 Office Action issued in connection with U.S. Appl. No. 12/890,272 (Exhibit 20).
Feb. 4, 2014 Applicant-Initiated Interview Summary issued in connection with U.S. Appl. No. 12/890,272 (Exhibit 21).
Feb. 21, 2014 Response filed in connection with U.S. Appl. No. 12/890,272 (Exhibit 22).
Oct. 20, 2014 Office Action issued in connection with U.S. Appl. No. 12/890,272 (Exhibit 23).
Dec. 5, 2014 Applicant-Initiated Interview Summary issued in connection with U.S. Appl. No. 12/890,272 (Exhibit 24).
Jan. 12, 2015 Response filed in connection with U.S. Appl. No. 12/890,272 (Exhibit 25).
Apr. 24, 2015 Notice of Allowance issued in connection with U.S. Appl. No. 12/890,272 (Exhibit 26).
May 23, 2017 Supplemental Response filed in connection with U.S. Appl. No. 12/920,815 (Exhibit 27).
Mar. 22, 2017 Applicant-Initiated Interview Summary issued in connection with U.S. Appl. No. 12/920,815 (Exhibit 28).
Mar. 11, 2016 Supplemental Response filed in connection with U.S. Appl. No. 12/920,815 (Exhibit 29).
Mar. 7, 2016 Examiner-Initiated Interview Summary issued in connection with U.S. Appl. No. 12/920,815 (Exhibit 30).
Jan. 20, 2016 Examiner-Initiated Interview Summary issued in connection with U.S. Appl. No. 12/920,815 (Exhibit 31).
Dec. 18, 2015 Summary of Nov. 12, 2015 Examiner Interview filed in connection with U.S. Appl. No. 12/920,815 (Exhibit 32).
Nov. 18, 2015 Applicant-Initiated Interview Summary issued in connection with U.S. Appl. No. 12/920,815 (Exhibit 33).
Feb. 4, 2013 Applicant-Initiated Interview Summary issued in connection with U.S. Appl. No. 12/920,815 (Exhibit 34).
Jun. 7, 2016 Office Action, issued in connection with U.S. Appl. No. 14/738,639 (Exhibit 35).
Nov. 16, 2016 Response, filed in connection with U.S. Appl. No. 14/738,639 (Exhibit 36).
Dec. 1, 2016 Interview Summary, issued in connection with U.S. Appl. No. 14/738,639 (Exhibit 37).
Feb. 28, 2017 Summary of Examiner Interview and Communication Forwarding Terminal Disclaimer, filed in connection with U.S. Appl. No. 14/738,639 (Exhibit 38).
Mar. 7, 2017 Notice of Allowance, issued in connection with U.S. Appl. No. 14/738,639 (Exhibit 39).
Jun. 7, 2010 Office Action, issued in connection with U.S. Appl. No. 12/370,972 (Exhibit 40).
Dec. 6, 2010 Response, filed in connection with U.S. Appl. No. 12/370,972 (Exhibit 41).
Feb. 2, 2011 Final Office Action, issued in connection with U.S. Appl. No. 12/370,972 (Exhibit 42).
Jul. 5, 2011 Notice of Appeal, filed in connection with U.S. Appl. No. 12/370,972 (Exhibit 43).
Nov. 7, 2011 Response, filed in connection with U.S. Appl. No. 12/370,972 (Exhibit 44).
Jul. 18, 2013 Response, filed in connection with U.S. Appl. No. 12/370,972 (Exhibit 45).
Feb. 4, 2014 Applicant-Initiated Interview Summary issued in connection with U.S. Appl. No. 12/370,972 (Exhibit 46).
Feb. 21, 2014 Response, filed in connection with U.S. Appl. No. 12/370,972 (Exhibit 47).
Oct. 17, 2014 Office Action, issued in connection with U.S. Appl. No. 12/370,972 (Exhibit 48).
Dec. 8, 2014 Interview Summary, issued in connection with U.S. Appl. No. 12/370,972 (Exhibit 49).
Jan. 12, 2015 Response, filed in connection with U.S. Appl. No. 12/370,972 (Exhibit 50).
Apr. 10, 2015 Notice of Allowance, issued in connection with U.S. Appl. No. 12/370,972 (Exhibit 51).
Jun. 16, 2005 Response, filed in connection with U.S. Appl. No. 10/631,415 (Exhibit 52).
Aug. 11, 2016 Office Action issued in connection with U.S. Appl. No. 15/133,055 (Exhibit 53).
Nov. 11, 2016 Response filed in connection with U.S. Appl. No. 15/133,055 (Exhibit 54).
Feb. 14, 2017 Office Action issued in connection with U.S. Appl. No. 15/133,055 (Exhibit 55).
Jun. 13, 2017 Response filed in connection with U.S. Appl. No. 15/133,055 (Exhibit 56).
Jun. 14, 2017 Notice of Appeal filed in connection with U.S. Appl. No. 15/133,055 (Exhibit 57).
Jul. 17, 2017 Notice of Panel Decision from Pre-Appeal Brief Review issued in connection with U.S. Appl. No. 15/133,055 (Exhibit 58).
Jul. 19, 2017 Advisory Action issued in connection with U.S. Appl. No. 15/133,055 (Exhibit 59).
Nov. 15, 2017 Response filed in connection with U.S. Appl. No. 15/133,055 (Exhibit 60).

(56) References Cited

OTHER PUBLICATIONS

Jul. 19, 2018 Office Action issued in connection with U.S. Appl. No. 15/133,055 (Exhibit 61).
Nov. 19, 2018 Response to Jul. 19, 2018 Office Action issued in connection U.S. Appl. No. 15/133,055 (Exhibit 62).
Dec. 31, 2018 Office Action issued in connection with U.S. Appl. No. 15/616,679 (Exhibit 63).
Israeli Office Action dated Jun. 1, 2011 in connection with Israeli Patent Application No. 191566 (Exhibit 11).
Response filed to Australian Examiner's Report filed on Oct. 18, 2011 in connection with Australian Application No. 2006320559 (Exhibit 23).
Second Australian Examiner's Report dated Nov. 17, 2011 in connection with Australian Application No. 2006320559 (Exhibit 24).
Radford et al. (1995) Cancer Resarch (55) pp. 5180-5183) (Exhibit 43).
Schwarz et al. (2002) "Evidence that siRNAs Function as Guides, Not Primers, in the *Drosophila* and Human RNAi Pathways" Mol. Cell 10:537-548 (Exhibit 51).
Schwarz and Zamore (2002) "Why do miRNAs live in the miRNP?" Genes & Dev. 16:1025-1031 (Exhibit 52).
Spurdle, Amanda B., et al. "Prohibitin 3' untranslated region polymorphism and breast cancer risk in Australian women." The Lancet 360.9337 (2002): 925-926 (Exhibit 56).
Stark et al. (2003) "Identification of *Drosophila* MicroRNA Targets" PLoS Biol. 1:E60 (Exhibit 58).
Zeng et al. (2003) "MicroRNAs and small interfering RNAs can inhibit mRNA expression by similar mechanisms" Proc. Natl. Acad. Sci. USA 100:9779-9784 (Exhibit 77).
NCBI SNP Database ss 2981582, https://www.ncbi.nlm.nih.gov/projects/SNP/snp_ref.cgi?rs=2981582 downloaded Jun. 29, 2003 (Exhibit 81).
NCBI SNP Database ss 23920837 (rs889312), http://www.ncbi.nlm.nih.gov/projects/SNP/snp_ref.cgi?rs=889312, downloaded Aug. 20, 2004(Exhibit 82).
AFD Eur panel-North America perlegen (www.ncbi.nlm.nih.gov/projects/SNP/snp_viewTable.cgi?pop=1371)(Exhibit 3).
Amarzguioui et al. (2003) "Tolerance for mutations and chemical modifications in a siRNA" Nucl. Acids Res. 31:589-595 (Exhibit 6).
Antoniou, et al. (2008) "Common Breast Cancer-Predisposition Alleles are Associated with Breast Cancer Risk in BRCA1 and BRCA2 Mutation Carriers" American Journal of Human Genetics 82:937-948 (Exhibit 10).
Bonnen et al. (2002), Haplotype and Linkage Disequilibrium Architecture for Human Cancer-Associated Genes, Genome Research, 12:1846-1853 (Exhibit 15).
The Breast Cancer Association Consortium (2006) "Commonly Studied Single-Polymorphisms and Breast Cancer: Results from the Breast Cancer Association Consortium" Journal of National Cancer Institute 98:1382-1896 (Exhibit 16).
Caplen et al. (2001) "Specific inhibition of gene expression by small double-stranded RNAs in invertebrate and vertebrate systems" Proc. Natl. Acad. Sci. USA 98:9742-9747 (Exhibit 19).
CHEK 2 Breast Cancer consortium (2002) "Low-penetrance susceptibility to breast cancer due to CHEK2(*)1100deIC in noncarriers of BRCA1 or BRCA2 mutations" Nature Genetics 31: 55-59 (Exhibit 22).
Cox, A., et al. (2007) "A common coding variant in CASP8 is associated with breast cancer risk" Nature Genetics 39(3):352-358 (Exhibit 25).
Czauderna et al. (2003) "Structural variations and stabilising modifications of synthetic siRNAs in mammalian cells" Nucl Acids Res 31:2705-2716 (Exhibit 27).
Collaborative Group in Hormonal Factors in Breast Cancer (2001) "Familial breast cancer: collaborative reanalysis of individual data from 52 epidemiological studies including 58,209 women with breast cancer and 101,986 women without the disease" The Lancet 358:1389-1399 (Exhibit 28).

Dite et al. "Breast cancer risk prediction using clinical models and 77 independent risk-associated SNPs for women aged under 50 years: Australian Breast Cancer Family Registry." Cancer Epidemiology Biomarkers & Prevention 25.2 (2016): 359-365 (Exhibit 31).
Doench et al. (2003) "siRNAs can function as miRNAs" Genes & Dev. 17:438-442 (Exhibit 34).
Dunning, et al. (1999) "A systematic review of genetic polymorphisms and breast cancer risk" Cancer Epidemiology Biomarkers & Prevention 8:843-854 (Exhibit 35).
Dunning, et al. (2003) "A Transforming Growth Factor 1 Signal Peptide Variant Increases Secretion inVitro and Is Associated with Increased Incidence of Invasive Breast Cancer" Cancer Research 63:2610-2615 (Exhibit 36).
Easton (1999) "How many more breast cancer predisposition genes are there?" Cancer Research 1:1-4 (Exhibit 39).
Elbashir et al. (2002) "Analysis of gene function in somatic mammalian cells using small interfering RNAs" Methods 26:199-213 (Exhibit 41).
Fibroblast growth factor receptor 2, bacteria-expressed kinase, keratino dysostosis 1, crouzon syndrome, Pfeiffer syndrome, gene card for FGFR2, GC10M122473, pp. 1-17, available at www.genecards.org/cgi-din/carddisp.pl?gene=FGFR@&search=FGFR (Exhibit 42).
Finnegan et al. (1996) "Reduced DNA methylation in *Arabidopsis thaliana* results in abnormal plant development" Proc Natl Acad Sci USA 93:8449-8454 (Exhibit 43).
Goodchild (1990) "Conjugates of Oligonucleotides and Modified Oligonucleotides: A Review of Their Synthesis and Properties" Bioconjugate Chem. 1:165 (Exhibit 45).
Hanks, et al (2003) Genome Biology vol. 4, p. 11 published Apr. 29, 2003 (Exhibit 47).
Kalemi, et al. (2005) "The association of p53 mutations and p53 codon 72, Her 2 codon 655 and MTHFR C677T polymorphisms with breast cancer in Northern Greece" Cancer Letters 222(1): 57-65 (Exhibit 67).
Kim et al. (2005) "Synthetic dsRNA Dicer substrates enhance RNAi potency and efficacy" Nature Biotechnology 23:222-226 (Exhibit 70).
Kohler and Milstein (1975) "Continuous cultures of fused cells secreting antibody of predefined specificity" Nature 256:495-497 (Exhibit 71).
Lichtenstein, et al. (2000) "Environmental and Heritable Factors in the Causation of Cancer—Analyses of Cohorts of Twins from Sweden, Denmark, and Finland" New England Journal of Medicine 343(2):78-85 (Exhibit 77).
Listgarten et al. (2004) "Predictive Models for Breast Cancer Susceptibility from Multiple Single Nucleotide Polymorphisms" Clinical Cancer Research 10(8):2725-2737 (Exhibit 78).
Mattick and Makunin (2005) "Small regulatory RNAs in mammals" Hum. Mol. Genet. 14:R12-R132 (Exhibit 80).
Meister et al. (2004) "Sequence-specific inhibition of microRNA and siRNA-induced RNA silencing" RMA 10:544-550 (Exhibit 84).
Morrison et al. (1984) "Chimeric human antibody molecules: Mouse antigen-binding domains with human constant region domains" Proc. Natl. Acad. Sci. USA 81:6851-6855 (Exhibit 88).
Response filed to Second Australian Examiner's Report filed 7 Dec. 2011 in connection with Australian Application No. 2006320559 (Exhibit 25).
English language translation of Notice from Chinese Patent Office issued Jun. 1, 2011 in connection with Chinese Patent Application No. 200680051710.0 (Exhibit 26).
Response filed to Chinese Notice on Jul. 25, 2011 in connection with Chinese Patent Application No. 200680051710.0, including English Language claims (Exhibit 27).
English language translation of First Chinese Office Action issued Oct. 13, 2011 in connection with Chinese Patent Application No. 200680051710.0 (Exhibit 28).
Response filed to First Chinese Office Action dated Feb. 9, 2012 in connection with Chinese Patent Application No. 200680051710.0, including English Language claims (Exhibit 29).

(56) References Cited

OTHER PUBLICATIONS

Response filed to Japanese Office Action dated Aug. 24, 2012 in connection with Japanese Patent Application No. 2008-543446, including English Language claims (Exhibit 32).
Japanese Patent Application Publication No. JP 2005/532780, published Nov. 4, 2005 (Ralph et al.), corresponding to PCT International Publication No. WO 2003/025141 (Exhibit 33).
Japanese Patent Application Publication No. JP 2001/503276, published Mar. 13, 2001 (Jupe et al.) corresponding to PCT International Publication No. WO 1998/20167 (Exhibit 34).
Patil, et al. "Blocks of Limited Haplotype Diversity Revealed by High-Resolution Scanning of Human Chromosome 21" (2001) Science 294(5547):1719-1723 (Exhibit 37).
Peto, et al. (1999) "Prevalence of BRCA1 and BRCA2 Gene Mutations in Patients With Early-Onset Breast Cancer" Journal of the National Cancer Institute 91(11):943-949 (Exhibit 38).
Pharoah, et al. (2002) "Polygenic susceptibility to breast cancer and implications for prevention" Nature Genetics 31:33-36 (Exhibit 39).
Adami, et al. (1998) "Towards an understanding of breast cancer etiology" Cancer Biology 8:255-262 (Exhibit 1);.
Adnane, et al. (1991) "BEK and FLG, two receptors to members of the FGF family, are amplified in subsets of human breast cancers" Onogene 6(4):659-663 (Exhibit 2);.
AFD Eur Panel-North America perlegen (www.ncbi.nlm.nih.goc/projects/SNP/snp_viewTable.cgi?pop=1371) (Exhibit 3);.
Agami (2002) "RNAi and related mechanisms and their potential use for therapy" Curr Opin Chem Biol 6:829-834 (Exhibit 4);.
Agúndez (2004) "Cytochrome P450 gene polymorphism and cancer." Current drug metabolism 5: 211-224 (Exhibit 5);.
Amarzguioui et al. (2003) "Tolerance for mutations and chemical modifications in a siRNA" Nucl. Acids Res. 34:589-595 (Exhibit 6);.
The Anglian breast cancer study group, (2000) "Prevalence and penetrance of BRCA1 and BRCA2 mutations in a population-based series of breast cancer cases" British Journal of Cancer 83(10):1301-1308 (Exhibit 7);.
Antoniou, et al. (2003) "Average risks of breast and ovarian cancer associated with BRCA1 or BRCA2 mutations detected in case Series unselected for family history: a combined analysis of 22 studies" American Journal of Human Genetics 72:1117-1130 (Exhibit 8);.
Antoniou, et al. (2001) "Evidence for further breast cancer susceptibility genes in addition to BRCA1 and BRCA2 in a population-based study" Genetic Epidemiology 21:1-18 (Exhibit 9);.
Antoniou, et al. (2008) "Common Breast Cancer-Predisposition Alleles and Associated with Breast Cancer Risk in BRCA1 and BRCA2 Mutation Carriers" American Journal of Human Genetics 82:937-948 (Exhibit 10);.
Bartel and Bartel (2003) "MicroRNAs: At the Root of Plant Development?" Plant Physiology 132:709-717 (Exhibit 11);.
Beaucage and Iyer (1993) "The Synthesis of Modified Oligonucleotides by the Phosphoramidite Approach and Their Applications" Tetrahedron 49:6123 (Exhibit 12);.
Becker et al. (1995) "Combined mapping of AFLP and RFLP markers in barley" Mol Gen Genet 249:65 (Exhibit 13);.
Bird (1988) "Single-Chain Antigen-Binding Proteins" Science 242:423-426 (Exhibit 14);.
Bonnen et al. (2002), Haplotype and Linkage Disequilibrium Architecture for Human Cancer-Associated Genes, Genome Research, 12:1846-4853 (Exhibit 12);.
The Breast Cancer Association Consortium (2006) "Commonly Studied Single-Neucleotide Polymorphisms and Brest Cancer: Results from the Breast Cancer Association Consortium" Journal of National Cancer Institute 98:1382-1896 (Exhibit 16);.
Campbell, Ian G., James Allen, and Diana M. Eccles. "Prohibitin 3' untranslated region polymorphism and breast cancer risk." Cancer Epidemiology Biomarkers & Prevention 12.11 (2003) : 1273-1274 (Exhibit 17);.
Canzian, F., et al. (2006) "Polymorphisms of genes coding for insulin-like growth factor 1 and its major binding proteins, circulating levels of IGF-1 and IGFBP-3 and breast cancer risk: results from EPIC study" British Journal of Cancer 94:299-307 (Exhibit 18);.
Caplen et al. (2001) "Specific inhibition of gene expression by small double-stranded RNAs in invertebrate and vertebrate sysmes" Proc. Natl. Acad. Sci. USA 98:9742-9747 (Exhibit 19);.
Carlson, et al. (2004) "Selecting a maximally informative set of single-nucleotide polymorphisms for association analyses using linkage disequilibrium" American Journal of Human Genetics 74:106-120 (Exhibit 20);.
Chapman, et al. (2003) "Detecting disease associations due to linkage disequilibrium using haplotype tags: a class of tests and the determinants of statistical power" Human Heredity 56:18-31 (Exhibit 21);.
Chek 2 Breast Cancer consortium (2002) "Low-penetrance susceptibility to breast cancer due to CHEK2(*)1100delC in noncarriers of BRCA1 or BRCA2 mutations" Nature Genetics 31: 55-59 (Exhibit 22);.
Chlebowski, R., et al. (2002) "American Society of Clinical Oncology Technology Assessment of Pharmacologic Interventions for Breast Cancer Risk Reduction Including Tamoxifen, Raloxifene, and Aromatase Inhibition" Journal of Clinical Oncology 20(15):3328-3343 (Exhibit 23);.
Cote et al. (1983) "Specific inhibition of gene expression by small double-stranded RNAs in invertebrate and vertebrate systems" Proc. Natl. Acad. Sci. USA 80:2026-2030 (Exhibit 24);.
Cox, A., et al. (2007) "A common coding cariant in CASP8 is associated with breast cancer irsk" Nature Genetics 39(3):352-358 (Exhibit 25);.
Cui, et al. (2001) "After BRCA1 and BRCA2—what next? Multifactorial segregation analyses of three-generation, population-based Australian Families affected by female breast cancer" American Journal of Human Genetics 68:420-431 (Exhibit 26);.
Czauderna et al. (2003) "Structural variaiton and stabilising modifications of synthetic siRNAs in mammalian cells" Nucl Acids Res 31:2705-2716 (Exhibit 27);.
Collaborative Group in Hormonal Factors in Breast Cancer (2001) "Familial breast cancer: collaborative reanalysis of indicidual data from 52 epidemiological studies inculdig 58, 209 women with breast cancer and 101,986 women without the disease" The Lancet 358:1389-1399 (Exhibit 28);.
Day et al. (1999) "EPIC-Norfolk: study design and characteristics of the cohort" British Journal of Cancer 80(1):95-103 (Exhibit 29);.
Deloukas et al. (2004) " The DNA sequence and comparative analysis of human chromosome 10" Nature, 429: 375-381 (Exhibit 30);.
Dite et al. "Breast cancer risk prediction using clinical models and 77 independent risk-associated SNPs for women aged under 50 years: Australian Breast Cancer Family Registry."Cancer Epidemiology Biomarkers & Prevention 525.2 (2006): 259-365 Exhibit 31);.
Dite, G. et al., "Value of adding single-nucleotide polymorphism panel markers to phenotypic algorithms of breast cancer risk", Cancer Research, May 2015, vol. 75, No. 9 suppl. 1, abstract No. P6-09-05 (Exhibit 32);.
Doench and Sharp (2004) "Specificity of microRNA target selection in translational repression" Genes & Dev. 18:504-511 (Exhibit 33);.
Doench et al. (2003) "siRNAs can function as miRNAs" Genes & Dev. 14-438-442 (Exhibit 34);.
Dunning, et al. (1999) "A systematic review of genetic polymorphisms and breast cancer risk" Cancer Epidemiology Biomarkers & Preventipn 8:843-854 (Exhibit 35);.
Dunning, et al. (2003) "A Transforming Growth Factor 1 Signal Peptide Variant Increases Secretion inVitro and Is Associated with Increased Incidence of Invasive Breast Cancer" Cancer Research 63:2610-3615 (Exhibit 36);.
Dunning, et al. (2004) "Polymorphisms Associated With Circulating Sex Hormone Levels in Postmenopausal Women" Journal of National Cancer Institute 96(12):936-945 (Exhibit 37);.
Dykxhoorn et al. (2003) "Killing the Messenger: Short RNAs that Silence Gene Expression" Nature Reviews Molec. and Cell Biol. 4:457-467 (Exhibit 38);.
Easton (1995) "How man more breast cancer predispisition genes are there?" Cancer Research 1:1-4 (Exhibit 39);.

(56) References Cited

OTHER PUBLICATIONS

Elbashir et al. (2001) "Duplexes of 21-nucleotide RNAs mediate RNA interference in cultured mammalian cells" Nature 411:494-498 (Exhibit 40);.
Elbashir et al. (2002) "Analysis of gene function inn somatic mammalian cells using small interfering RNAs" Methods 26:199-213 (Exhibit 41);.
Fibroblast growth factor receptor 2, bacteria-expressed kinase, keratino dysostosis 1, crouzon syndrome, Pfeiffer syndrome, gene and card for FGFR2, GC10M122473, pp. 1-17, available at www.genecards.org/cgi-din/carddisp.pl?gene=FGFR@&search=FGFR (Exhibit 42);.
Finnegan et al. (1996) "Reduced DNA methylation in Arabipopsis thaliana results in abnormal plant development" Proc Natl Acad Sci USA 93:8449-8454 (Exhibit 43);.
Ford, et al. (1998) "Genetic Heterogeneity and Penetrance Analysis of the BRCA1 and BRCA2 Genes in Breast Cancer Families" American Journal of Human Genetics 62:676-689 (Exhibit 44);.
Goodchild (1990) "Conjugates of Oligonucleotides and Modified Oligonucleotides: A Review of Their Synthesis and Properites" Bioconjugate Chem. 1:165 (Exhibit 45);.
Goode, et al. (2001) Genetic Epidemiology 126: p. 155 (Exhibit 46);.
Hanks, et al (2003) Genome Biology vol. 4, p. 11 published Apr. 23, 2003 (Exhibit 47);.
Hannon (2002) "RNA interference" Nature 418:244 30:251 (Exhibit 48);.
Healey, et al. (2000) "A common variant in BRCA2 is associated with both breast cancer risk and prenatal viability" Nature Genetics 26:362-364 (Exhibit 49);.
Heiskanen, et al. (2001) "CGH, cDNA and tissue microarray analyses implicate FGFR2 amplification in a small subset of breast tumors" Analytical Cellular Pathology 22: 229-234.(Exhibit 50);.
Hinds, et al. (2005) "Whole-genome patterns of common DNA variation in three human populations" Science 307:1072-1079. (Exhibit 51);.
Hirschhorn et al. (Genetics in Medicine. vol. 4, No. 2, pp. 45-61, Mar. 2002) (Exhibit 52);.
Holen et al. (2003) "Similar behaviour of single-strand and double-strand siRNAs suggests they act through a common RNAi pathway" Nucl. Acids Res. 31:2401-2407 (Exhibit 53);.
Hunter et al. (2007) "A genome-wide association study identifies alleles in FGFR2 associated with risk of sporadic postmenopausal breast cancer" Nature Genetics (2007) 39(6):870-874 (Exhibit 54);.
Huse et al. (1989) "Generation of a Large Combinatorial Library of the Immunoglobulin Repertoire in Phage Lambda" Science 246:1275-1281 (Exhibit 55);.
Huston et al. (1988) "Protein engineering of antibody binding sites: Recovery of specific activity in an anti-digoxin single-chain Fv analogue produced in Escherichia coli" Proc. Natl. Acad. Sci. USA 85:5879-5883 (Exhibit 56);.
Hutvagner and Zamore (2002) "RNAi: nature abhors a double-strand" Curr Opin Genet & Dev 200:225-232 (Exhibit 57);.
Huusko, et al. (2004) "Genome-wide scanning for linkage in Finnish breast cancer families" European Journal of Human Genetics 12: 98-104 (Exhibit 58);.
Huusko, "Genome-wide scanning for linkage in Finnish breast cancer families" European Journal of Human Genetics 12:256 (2003) (Exhibit 59);.
Ioannidis (2001) "Replication validity of genetic association studies" Nature Genetics 29:306-309 (Exhibit 60);.
Ishibe et al. (1998) Cancer Research 58: 667-671 (Exhibit 61);.
Issaq et al. (2003) "SELDI-TOF MS for Diagnostic Proteomics" Analytical Chemistry 75:149A-155A (Exhibit 62);.
Kohno et al (2001), Medical Online 6:25-31* (Exhibit 63);.
Jang, et al. (2001) "Mutations in Fibroblast •growth factor receptor 2 and fibroblast growth factor receptor 3 genes associated with human gastric and colorectal cancers" Cancer Research 61: 3541-3543 (Exhibit 64);.

Jorde (2000) "Linkage Disequilibrium and the Search for Complex Disease Genes" Genome Research 10:1435-1444 (Exhibit 65);.
Kamali-Sarvestani, et al. (2005) "Polymorphism in genes of alpha and beta tumor necrosis factors (TNF-α and TNG-β and gamma interferon (IFN-γ) among Iranian women and breast cancer" Cancer Letters 223(1): 113-119 (Exhibit 66);.
Kalemi, et al. (2005) "The association of p53 mutations and p53 codon 72, Her 2 codon 655 and Mthfr C677T polymorphisms with breast cancer in Northern Greece" Cancer Letters 222(1): 57-56 (Exhibit 67);.
Katoh & Katoh, (2003) "FGFR2 and WDR11 are neighboring oncogene and tumor suppressor gene on human chromosome 10q26" International Journal of Oncology 22:1155-2737 (Exhibit 68);.
Kawasaki and Taira (2004) "Induction of DNA methylation and gene silencing by short interfering RNAs in human cells" Nature 431:211-217 (Exhibit 69);.
Kim et al. (2005) "Synthetic dsRNA Dicer substrates enhance RNA: potency and efficacy" Nature Biotechnology 23:222-226 (Exhibit 70);.
Kohler and Milstein (1975) "Continuous cultures of fused cells secreting antibody of predefined specificiy" Nature 256:495-497 (Exhibit 71);.
Kosbor et al. (1983) "The production of monoclonal antibodies from human lymphocytes" Immunology Today 4:72 (Exhibit 72);.
Kuschel, et al. (2002) "Variants in DNA double-strand break repair genes and breast cancer susceptibility" Human Molecular Genetics 11(12):1399-1407 (Exhibit 73);.
Laan et al. (1997) Nature Genetics 17:435-438 (Exhibit 74);.
Lee, et al. (2005) "Genetic polymorphisms of ataxia telangiectasia mutated and breast cancer risk" Cancer Epidemiology, Biomarkers & Prevention 14(4):821-825 (Exhibit 75);.
Lesueur et al. (2005) "Allelic association of the human homologue of the mouse modifier Ptprj with breast cancer" Human Molecular Genetics 14:2349 (Exhibit 76);.
Lichtenstein, et al. (2000) "Environmental and Heritable Factors in the Causation of Cancer—Analyses of Cohorts of Twins from Sweden, Denmakr, and Finland" New England Journal of Medicine 343(2):78-85 (Exhibit 77);.
Lisgarten et al. (2004) "Predictive Models for Breast Cancer Susceptibility from Multiple Single Nucleotide Polymorphisms" Clinical Cancer Research 10(8):2725-2737 (Exhibit 78);.
Martinez et al. (2002) "Single-Stranded Antisense siRNAs Guide Target RNA Cleavage in RNAi" Cell 110:563-574 (Exhibit 79);.
Mattick and Makunin (2005) "Small regulatory RNAs in mammals" Hum. Mol. Genet. 14:R121-R132 (Exhibit 80);.
Maxwell et al. (2013), "Common breast cancer risk variants in the post-Cogs era: a comprehensive review", Breast Cancer Research, 15:212 (Exhibit 81);.
McManus (2003) "MicroRNAs and cancer" Semin Cancer Biol. 13:253-288 (Exhibit 82);.
McManus and Sharp (2002) "Gene Silencing in Mammals by Small Interfering RNAS" Nature Reviews Genetics 3:737-747 (Exhibit 83);.
Meister et al. (2004) "Sequence-specific inhibition of microRNA and siRNA-induced Rna silencing" RNA 10:544-550 (Exhibit 84);.
Meksem et al. (1995) "A high-resolution map of the vicinity of the R1 locus on chromosome V of potato based on RFLP and AFLP markers" Mol Gen Genet 249:74 (Exhibit 85);.
Moffa, et al. (2004) "Transforming potential of alternatively spliced variants of fibroblast growth factor receptor 2 in human mammary epithelial cells" Molecular Cancer Research 2(11): 643-652 (Exhibit 86);.
Morris et al. (2004) "Small Interfering Rna-Induced Transcriptional Gene Silencing in Human Cells" Science 305:1289-1292 (Exhibit 87);.
Morrison et al. (1984) "Chimeric human antibody molecules: Mouse antigen-binding domains with human constant region domains" Proc. Natl. Acad. Sci. USA 81:6851-6855 (Exhibit 88); and.
Nelson et al. (2003) "The microRNA world: small is mighty" Trends Biochem. Sci. 28:534-540 (Exhibit 89).
PCT International Application Publication No. WO 98/020167 published May 14, 1998 (Oklahoma Medical Research Foundation) (Exhibit 1);.

(56) References Cited

OTHER PUBLICATIONS

PCT International Search Report dated Dec. 6, 2007 in connection with PCT International Application No. PCT/US2006/045812, filed Nov. 29, 2006 (Exhibit 2);.
PCT International Application Publication No. WO 95/011995, published May 4, 1995 (Chee et al.) (Exhibit 3);.
PCT International Application Publication No. WO 2005/024067, published Mar. 17, 2005 (Ralph et al.) (Exhibit 4);.
PCT International Publication No. WO 2003/025141, published Mar. 27, 2003 (Ralph et al.) (Exhibit 5);.
PCT International Application Publication No. WO 00/33161, published Jun. 8, 2000 (Rienhoff et al.) (Exhibit 6);.
PCT International Application Publication No. WO 2005/086770 A3, published Sep. 22, 2005 (Cox et al.) (Exhibit 7);.
PCT International Search Report dated Dec. 8, 2015 in connection with International Application No. PCT/AU2015/050583 (Exhibit 8).
English language translation of Israeli Office Action dated Jul. 14, 2010 in Connection with Israeli Patent Application No. 191566 (Exhibit 9);.
Response filed to Israeli Office Action filed Nov. 9, 2010 in connection with Israeli Patent Application No. 191566, including English language translation of transmittal letter (Exhibit 10);.
Israeli Office Action dated Jun. 1, 2011 in connection with Israeli Patent Application No. 191566 (Exhibitt 11);.
Response filed to Israeli Office Action filed Oct. 2, 2011 in connection with ISraeli Patent Application No. 191566 (Exhibit 12);.
English language translation of Israeli Office Action dated Feb. 29, 2012 in connection with Israeli Patent Application No. 191566 (Exhibit 13);.
English language translation of Response filed to Israeli Office Action dated Jun. 20, 2012 in connection with Israeli Patent Application No. 191566 (Exhibit 14);.
European Search Opinion dated Oct. 13, 2009 in connection with European Patent Application No. 06838661.4 (Exhibit 15);.
Response to Examination report dated Feb. 12, 2010 in connection with European Patent Application No. 06838661.4 (Exhibit 16);.
Response filed to European Examination Report filed Aug. 23, 2010 in connection with European Patent Application No. 06838661.4 (Exhibit 17);.
Examination Report dated Feb. 17, 2012 in connection with European Patent Application No. 06838661.4 (Exhibit 18);.
Response filed to European Examination Report dated Feb. 22, 2012 in connection with European Patent Application No. 06838661.4 (Exhibit 19).
Apr. 9, 2018 Extended European Search Report issued by the European Patent Office (EPO) in connection with European Patent Application No. 15847907.1 (Exhibit 20);.
Kaklamani et al. (2013) "Adiponectin pathway polymorphisms and risk of breast cancer in African Americans and Hispanics in the Women's Health Initiative", Breast Cancer Res Treat. 139(2):461-468 (Exhibit 21);.
Australian Examiner's Report dated Jun. 29, 2011 in connection with Australian Application No. 2006320559 (Exhibit 22);.
Response filed to Australian Examiner's Report filed Oct. 18, 2011 in connection with Australian Application No. 2006320559 (Exhibit 23);.
Second Australian Examiner's Report dated Nov. 17, 2011 in conncetion with Australian Application No. 2006320559 (Exhibit 24);.
Response filed to Second Australian Examiner's Report filed Dec. 7, 2011 in connection with Australian Application No. 2006320559 (Exhibit 25);.
English language translation of Notice from Chinese Patent Office dated Jun. 1, 2011 in connection with Chinese Patent Application No. 200680051710.0 (Exhibit 26);.
Response filed to Chinese Notice on Jul. 25, 2011 in connection with Chinese Patent Application No. 200680051710.0, including English Language copy of claims (Exhibit 27);.
English language translation of First Chinese Office Action dated Oct. 13, 2011 in connection with Chinese Patent Application No. 200680051710.0 (Exhibit 28);.
Response filed to First Chinese Office Action dated Feb. 9, 2012 in connection with Chinese Patent Application No. 200680051710.0, including English Language copy of claims (Exhibit 29);.
English language translation of Second Chinese Office Action in connection with Chinese Patent Application No. 200680051710.0 (Exhibit 30);.
Japanese Office Action dated Feb. 22, 2012 in connection with Japanese Patent Application No. 2008/543446, including English language translation (Exhibit 31);.
Response filed to Japanese Office Aciton dated Aug. 24, 2012 in connection with Japanese Patent Application No. 2008/543446, including English language copy of claims (Exhibit 32);.
Japanese Patent Application No. JP 2005/532780, published Nov. 4, 2005 (Ralph et al.), corresponding to PCT International Publication No. WO 2003/025141 (Exhibit 33);.
Japanese Patent Application No. JP 2001/503276, published Mar. 13, 2001 (Jupe et al.) corresponding to PCT International Publication No. WO 1998/20167 (Exhibit 34).
Neuberger et al, (1984) "Recombinant antibodies possessing novel effector functions" Nature 312:604-608 (Exhibit 35);.
Nishikura (2001) "A Short Primer on RNAi: RNA-Directed RNA Polymerase Acts as a Key Catalyst" Cell 107:415-418 (Exhibit 36);.
Patil, et al. "Blocks of Limited Haplotype Diversity Revealed by High-Resolution Scanninng of Human Chromosome 21" (2001) Science 294(5547):1719-1723 (Exhibit 37);.
Peto, et al. (1999) "Precalence of BRCA1 and BRCA2 Gene Mutations in Patients with Early-onset Breast Cancer" Journal of the National Cancer Institute 91(11):943-949 (Exhibit 38);.
Pharoahh, et al. (2002) "Polygenic susceptibility to breast cancer and implications for precention" Nature Genetics 31:33-36 (Exhibit 39);.
Pharoah et al. (2004), Association Studies for Finding Cancer-Suceptibility Genetic Variants, Nature Reviews, 4:850-860 (Exhibit 40);.
Ponder et al. (2005), Polygenic Inherited Predisposition to Breast Cancer, Cold Spring Harbor Symposia on Quantitative Biology, vol. LXX, p. 35-41 (Exhibit 41);.
Pritchard, et al. (2001) "Linkage disequilibrium in humans: models and data" American Journal of Human Genetics 69:1-14 (Exhibit 42);.
Radford et al. (1995) Cancer Research (55) pp. 5180-5183) (Exhibit 43);.
Rehmsmeier et al. (2004) "Fast and effective prediction of microRNA/ target duplexes" RNA 10:1507-1517 (Exhibit 44);.
Robins et al. (2005) "Incorporating structure to predict microRNA targets" Proc. Natl. Acad. Sci. 102:4006-4009 (Exhibit 45);.
Sasieni (1997) "From genotypes to genes: doubling the sample size" Biometrics 53(4):1253-1261 (Exhibit 46);.
Satagopan, et al., (2002) "Two-stage designs for gene-disease association studies" Biometrics 58:163-170 (Exhibit 47);.
Scacheri et al. (2004) "Short interfering RNAs can induce unexpected and divergent changes in the levels of untargeted proteins in mammalian cells" Proc. Natl. Acad. Sci. USA 101:1892-1897 (Exhibit 48);.
Schmith et al. (2003) "Pharmacogenetics and disease genetics of complex diseases" CMLS Cell. Mol. Life Sci. 60:1636-1646) (Exhibit 49);.
Schramke and Allshire (2003) "Hairpin RNAs and Retrotransposon LTRs Effect RNAi and Chromatin-Based Gene Silencing" Science 301:1069-1074 (Exhibit 50);.
Schwartz et al. (2002) "Evidence that siRNAs Function as Guides, Not Primers, in the Drosophila and Human RNAi Pathways" Mol. Cell 10:537-548 (Exhibit 51);.
Schwarts and Zamore (2002) "Why do MiRNAs live in the MiRNP?" Genes & Dev. 16:1025-1031 (Exhibit 52);.
Sempere et al. (2004) "Expression profiling of mammalian microRNAs uncovers a subset of brain-expressed microRNAs with possible roles in murine and human neuronal differentiation" Genome Biology 5:R13 (Exhibit 53);.

(56) References Cited

OTHER PUBLICATIONS

Siolas et al. (2005) "Synthetic shRNAs as potent RNAi Triggers" Nature Biotechnology 23:227-231 (Exhibit 54);.
Sprecher Institute "Breast Cancer in Women from Different Racial/Ethnic Groups Fact Sheet #47" Apr. 2003 envirocancer.cornell.edu/Factsheet/general/fs47.ethnicity.cfm (Exhibit 55);.
Spurdle, Amanda B., et al. "Prohibition 3' untranslated region polymorphism and breast cancer risk in Australian women." The Lancet 360.9337 (2002): 925-926 (Exhibit 56);.
Stankovic, et al. (1998) "ATM mutations and phenotypes in ataxia-telangiectasia families in the British Isles: expression of mutant ATM and the risk of leukemia, lymphoma. and breast cancer" American Journal of Human Genetics 62:334-345 (Exhibit 57);.
Stark et al. (2003) "Identification of Drosphila MicroRNA Targets" PLoS Biol. 1:E60 (Exhibit 58);.
Stephens, et al. (2005) "A screen of the complete protein kinase gene family identifies diverse patterns of somatic mutations in human breast cancer" Nature Genetics 37:590-592 and supplemental information (Exhibit 59);.
Takashi et al. (2001) "3. Byouti Kaiseki to SNP 1 Gan (Pathologic Analysis and SNP, 1 Cancer)", Ketsueki/Meneki/Shuyou, 6(4):353-359 (Exhibit 60);.
Takeda et al. (1985) "Construction of chimaeric processed immunoglobulin genes containing mouse variable and human constant region sequences" Nature 314:452-454 (Exhibit 61);.
Tang et al. (2003) "A biochemical framework for RNA silencing in plants" Genes & Dev. 17:49-63 (Exhibit 62);.
Tang et al. (2005) "Genetic structure, self-identified race. Ethnicity and confounding in case-control association studies" Am. J. Hum. Genet. 76(2):268-275 (Exhibit 63);.
Tannheimer, et al. (2000) "Characterization of fibroblast growth factor receptor 2 overexpression in the human breast cancer cell line SUM-52PE" Breast Cancer Research 2:311-320. (Exhibit 64);.
Thompson, et al. (2002) "Evaluation of linkage of breast cancer to the putative BRCA3 locus on chromosome 13q21 in 128 multiple case families from the Breast Cancer Linkage Consortium" Proceedings of the National Academy of Sciences USA 99(2):827-831 (Exhibit 65);.
Tischkoff, et al. (2004) "Implications of biogeography of human populations for 'race' and medicine" Nature Genetics 36:s21-s27 (Exhibit 66);.
Titus-Ernstoff, et al. (1998) "Menstrual factors in relation to breast cancer risk" Cancer Epidemiology, Biomarkers & Prevention 7:783-789 (Exhibit 67);.
Tuschl and Borkhardt (2002) "Small Interfering RNAs: A revolutionary Tool for the Analysis of Gene Function and Gene Therapy" Molecular Interventions 2:158-167 (Exhibit 68);.
Uhlmann and Peyman (1990) "Antisense Oligonucleotides: A New Therapeutic Principle" Chem. Rev. 90:543 (Exhibit 69);.
Van't Veer et al. (2002) "Gene expression profiling predicts clinical outcome of breast cancer" Nature: International Weekly Journal of Science 415(6871):530-536 (Exhibit 70);.
Van de Vijver et al. (2002) "A Gene-expression signature as a predictor of survival in breast cancer" New England Journal of Medicine 347(25): 1999-2009 (Exhibit 71);.
Vos et al. (1995) "AFLP: a new technique for DNA fingerprinting" Nucl Acids Res 23:4407 (Exhibit 72);.
Wang et al. (2004) Cancer Research 64:64-71 (Exhibit 73);.
Ward et al. (1989) "Binding activities of repertoire of single immunoglobulin variable domains secreted from *Echerichia coli*" Nature 334:544-546 (Exhibit 74);.
Wall, et al. (2003) "Haplotype blocks and linkage disequilibrium in the human genome" Nature Reviews Genetics 4:587-597 (Exhibit 75);.
Zamore (2001) "RNA interference: listening to the sound of silence" Nature Structural Biology 8:746-750 (Exhibit 76);.
Zeng et al. (2003) "MicroRNAs and small interfering RNAs can inhibit mRNA expression by similar mechanisms" Proc. Natl. Sci. USA 100:9779-9784 (Exhibit 77);.
Zhang, et al. (2002) "A dynamic programming algorithm for haplotype block partitioning" Proceedings of the National Academy of Sciences USA 99(11):7335-7339 (Exhibit 78);.
*Enfish, LLC* v. *Microsoft Corp.*, No. 2015-1244 (Fed. Cir. May 12, 2016) (Exhibit 79);.
NCBI Database ss22777675, https://www.ncbi.nlm.nih.gov/projects/SNP/snp_ref.cgi?rs=76452710, downloaded on Mar. 21, 2004 (Exhibit 80);.
NCBI SNP Database rs 2981582, https://www.ncbi.nlm.nih.gov/projects/SNP/snp_ref.cgi?rs=2981582 downloaded Jun. 29, 2003 (Exhibit 81);.
NCBI SNP Database ss 23920837 (r5889312), http://www.ncbi.nlm.nih.gov/projects/SNP/snp_ref.cgi?rs.889312, downloaded Aug. 20, 2004 (Exhibit 82);.
May 19, 2016 Memorandum from USPTO Deputy Commissioner for patent Examination Policy to the Patent Examining Corps (Exhibit 83).

\* cited by examiner

METHODS FOR BREAST CANCER RISK ASSESSMENT

This application is a continuation of U.S. Ser. No. 12/920,815, a § 371 national stage of PCT International Application No. PCT/AU2010/000675, filed Jun. 1, 2010, claiming the benefit of U.S. Provisional Application Nos. 61/258,420, filed Nov. 5, 2009 and 61/182,809, filed Jun. 1, 2009.

REFERENCE TO SEQUENCE LISTING

This application incorporates-by-reference nucleotide and/or amino acid sequences which are present in the file named "171115_83732_A_Sequence_Listing_BI.txt," which is 5 kilobytes in size, and which was created Nov. 15, 2017 in the IBM-PC machine format, having an operating system compatibility with MS-Windows, which is contained in the text file filed Nov. 15, 2017 as part of this application.

FIELD OF THE INVENTION

The present invention relates to methods and systems for assessing the overall risk of a human female subject for developing a breast cancer phenotype. In particular, the present invention relates to combining clinical risk assessment and genetic risk assessment to improve risk analysis.

BACKGROUND OF THE INVENTION

Breast cancer, like other common cancers, shows familial clustering. Numerous epidemiological studies have demonstrated that, overall, the disease is approximately twice as common in first degree relatives of breast cancer patients. Family studies, and particularly twin studies, suggest that most if not all of this clustering has a genetic basis. For example, Peto and Mack (2000) estimated that the risk of breast cancer in the MZ twin of an affected woman was approximately four-fold greater than the risk to a sister of a case.

Several breast cancer susceptibility genes have already been identified, most importantly BRCA1 and BRCA2. Mutations in these genes confer a high risk of breast cancer (of the order of 65% and 45%, respectively, by age 70). Mutation screening of population-based series of breast cancer cases has shown that only about 15% of the familial risk of breast cancer can be explained by mutations in these genes. The other known breast cancer susceptibility genes (TP53, PTEN, ATM, CHEK2) make only small contributions to the familial risk (because the predisposing mutations are rare and/or confer only small risks). In total therefore, the known breast cancer susceptibility genes have been estimated to account for no more than 20% of the familial risk.

Genetic variation in risk may result from rare highly-penetrant mutations (such as those in BRCA1 and BRCA2) or from variants conferring more moderate risks. Several lines of evidence suggest strongly that high penetrance mutations are not major contributors to the residual familial risk of breast cancer. Firstly, mutation screening of multiple case families has found that the large majority of cases with a very strong family history (for example four or more affected relatives) harbor mutations in BRCA1 or BRCA2. Secondly, despite extensive efforts over the past nine years, genetic linkage studies have not identified any further linked loci. Thirdly, segregation analyses of large series of breast cancer families have found, after adjusting for BRCA1 and BRCA2, no evidence for a further major dominant breast cancer susceptibility allele. In a large analysis, Antoniou et al. (2009) found that the most parsimonious model for breast cancer was a polygenic model, equivalent to a large number of loci of small effect combining multiplicatively.

What is needed in the art, therefore, are further methods for assessing breast cancer susceptibility in female subjects.

SUMMARY OF THE INVENTION

The present invention relates to a method for assessing the overall risk of a human female subject for developing a breast cancer phenotype. Surprisingly, the authors have found that combining single nucleotide polymorphisms with a clinical risk assessment provides an advantage over using the clinical risk assessment in isolation. Thus, in a first aspect the present invention provides a method for assessing the overall risk of a human female subject for developing a breast cancer phenotype comprising:

performing a clinical risk assessment of the female subject;

performing a genetic risk assessment of the female subject, wherein the genetic risk assessment involves detecting, in a biological sample derived from the female subject, the presence at least two single nucleotide polymorphisms known to be associated with a breast cancer phenotype; and combining the clinical risk assessment with the genetic risk assessment to obtain the overall risk of a human female subject for developing a breast cancer phenotype.

The present invention is also useful for reclassifying subjects who have been analysed using a clinical risk assessment. Accordingly, in a further aspect the present invention provides a method of determining if the overall risk of a human female subject for developing a breast cancer phenotype analysed by clinical risk assessment should be reclassified, the method comprising combining the clinical risk assessment with a genetic risk assessment to obtain the overall risk of a human female subject for developing a breast cancer phenotype, wherein the genetic risk assessment involves detecting, in a biological sample derived from the female subject, the presence at least two single nucleotide polymorphisms known to be associated with a breast cancer phenotype, and determining if combining the clinical risk assessment with the genetic risk assessment results in a reclassification of the risk of the subject for developing a breast cancer phenotype.

In an embodiment, the net reclassification improvement (NRI) of the method is greater than 0.01, more preferably greater than 0.05, and even more preferably greater than 0.08. In a further embodiment, the NRI is about 0.09.

In an embodiment, the 5-year risk determined by the clinical risk assessment is between about 1.5% to about 2%. In this embodiment, it is preferred that the net reclassification improvement (NRI) of the method is greater than 0.1, more preferably greater than 0.12, and even more preferably greater than 0.15. In a further embodiment, the NRI is about 0.195.

Examples of suitable clinical risk assessment procedures include, but are not limited to, the Gail Model, the Claus model, Claus Tables, BOADICEA, the Jonker Model, the Claus Extended Formula, the Tyrer-Cuzick Model, and the Manchester Scoring System. Preferably, the clinical risk assessment is obtained using the Gail Model.

In an embodiment, the clinical risk assessment includes obtaining information from the female on one or more of the following: medical history of breast cancer, ductal carcinoma or lobular carcinoma, age, age of first menstrual period, age at which she first gave birth, family history of breast cancer, results of previous breast biopsies and race/ethnicity.

Preferably, the method comprises detecting the presence of at least three, four, five, six, seven, eight, nine or ten single nucleotide polymorphisms known to be associated with a breast cancer phenotype. More preferably, the method comprises detecting the presence of seven, eight, nine or ten single nucleotide polymorphisms known to be associated with a breast cancer phenotype.

In a preferred embodiment, the single nucleotide polymorphisms are selected from a group consisting of rs2981582, rs3803662, rs889312, rs13387042, rs13281615, rs4415084, and rs3817198, or a single nucleotide polymorphism in linkage disequilibrium with one or more thereof. In a further preferred embodiment, the single nucleotide polymorphisms are selected from a group consisting of rs2981582, rs3803662, rs889312, rs13387042, rs13281615, rs4415084, rs3817198, rs4973768, rs6504950 and rs11249433, or a single nucleotide polymorphism in linkage disequilibrium with one or more thereof. With regard to these two embodiments, it is preferred that the method comprises detecting the presence of at least three, four, five, six, seven, eight, nine or ten of the single nucleotide polymorphisms, more preferably seven, eight, nine or ten of the single nucleotide polymorphisms.

In an embodiment, the single nucleotide polymorphisms are individually tested for association with breast cancer by logistic regression under a log additive model with no covariates.

In another embodiment, the single nucleotide polymorphisms are tested in combination for association with breast cancer.

Preferably, combining the clinical risk assessment with the genetic risk assessment comprises multiplying the risk assessments.

The female can be of any race such as caucasian, negroid, australoid, or mongoloid. In a preferred embodiment, the female is caucasian. Preferably, the female is post-menopausal.

Surprisingly, the inventors have found that combining single nucleotide polymorphism analysis with clinical risk assessment provides a clear benefit in those women who have had a previous biopsy of the breast. Thus, in a preferred embodiment, the female has had a biopsy of the breast.

The inventors have also found that combining single nucleotide polymorphism analysis with clinical risk assessment provides a clear benefit in the possible reclassification of women whose clinical risk assessment indicates that they have a risk of developing breast cancer. Thus, in another preferred embodiment the results of the clinical risk assessment indicate that the female should be subjected to more frequent screening and/or prophylactic anti-breast cancer therapy.

In a further embodiment, if it is determined the subject has a risk of developing breast cancer using a method if the invention, the subject is more likely to be responsive oestrogen inhibition than non-responsive.

In a further aspect, the present invention provides a system for assessing the overall risk of a human female subject for developing a breast cancer phenotype comprising:
system instructions for performing a clinical risk assessment of the female subject;
system instructions for performing a genetic risk assessment of the female subject; and
system instructions for combining the clinical risk assessment with the genetic risk assessment to obtain the overall risk of a human female subject for developing a breast cancer phenotype.

Preferably, the system is a computer-implemented system.

In an embodiment, the system further comprises:
a set of marker probes or primers configured to detect, in a biological sample derived from the female subject, the presence of at least two single nucleotide polymorphisms known to be associated with a breast cancer phenotype;
a detector that is configured to detect one or more signal outputs from the set of marker probes or primers, or an amplicon produced from the set of marker probes or primers, thereby identifying the presence or absence of the at least two single nucleotide polymorphisms known to be associated with a breast cancer phenotype.

In an embodiment, the detector detects one or more light emissions, wherein the light emission is indicative of the presence or absence of the single nucleotide polymorphism.

In a further embodiment, the system comprises a biological sample derived from the female subject. In a further embodiment, the sample comprises genomic DNA, amplified genomic DNA, cDNA, amplified cDNA, RNA or amplified RNA.

In yet another aspect, the present invention provides a kit comprising at least two sets of primers for amplifying two or more nucleic acids, wherein the two or more nucleic acids comprise a single nucleotide polymorphism selected from a group consisting of rs2981582, rs3803662, rs889312, rs13387042, rs13281615, rs4415084, rs3817198, rs4973768, rs6504950 and rs11249433, or a single nucleotide polymorphism in linkage disequilibrium with one or more thereof.

Examples of primers suitable for a kit of the invention are provided in Table 6.

The kit may further comprise other reagents required to perform an amplification reaction such as a buffer, nucleotides and/or a polymerase, as well as reagents for extracting nucleic acids from a sample.

In a further aspect, the present invention provides a genetic array comprising at least two nucleic acids which independently comprise a single nucleotide polymorphism selected from a group consisting of rs2981582, rs3803662, rs889312, rs13387042, rs13281615, rs4415084, rs3817198, rs4973768, rs6504950 and rs11249433, or a single nucleotide polymorphism in linkage disequilibrium with one or more thereof.

Preferably, the array comprises nucleic acids representing each known allele of each SNP.

In a further aspect, the present invention provides a method for determining the need for routine diagnostic testing of a human female subject for breast cancer comprising assessing the overall risk of the subject for developing a breast cancer phenotype using a method of the invention.

In yet another aspect, the present invention provides a method of screening for breast cancer in a human female subject, the method comprising assessing the overall risk of the subject for developing a breast cancer phenotype using the method of the invention, and routinely screening for breast cancer in the subject if they are assessed as having a risk for developing breast cancer.

Examples of suitable methods of breast cancer screening include, but are not limited to, manual breast examination and mammography.

In a further aspect, the present invention provides a method for determining the need of a human female subject for prophylactic anti-breast cancer therapy comprising assessing the overall risk of the subject for developing a breast cancer phenotype using the method of the invention.

In yet a further aspect, the present invention provides a method for preventing breast cancer in a human female subject, the method comprising assessing the overall risk of the subject for developing a breast cancer phenotype using the method of the invention, and administering an anti-breast cancer therapy to the subject if they are assessed as having a risk for developing breast cancer.

Examples of suitable anti-breast cancer therapies include, but are not limited to, administration of tamoxifen or raloxifene.

In an embodiment, the therapy inhibits oestrogen.

In a further aspect, the present invention provides a method for stratifying a group of human female subjects for a clinical trial of a candidate therapy, the method comprising assessing the individual overall risk of the subjects for developing a breast cancer phenotype using the method of the invention, and using the results of the assessment to select subjects more likely to be responsive to the therapy.

As will be apparent, at least some features of the methods, kits and systems can be used together in combination. For example, systems for detecting modulators can be used for practicing methods of modulator detection. Systems for identifying correlations between breast cancer phenotype susceptibility and polymorphisms can be used for practicing the methods herein. Kits can be used for practicing the methods herein. Thus, described features of the systems, methods and kits can be applied to the different systems, methods and kits herein.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The invention is hereinafter described by way of the following non-limiting Examples and with reference to the accompanying figures.

BRIEF DESCRIPTION OF THE ACCOMPANYING DRAWINGS

DETAILED DESCRIPTION OF THE INVENTION

General Techniques and Definitions

Figure 1:
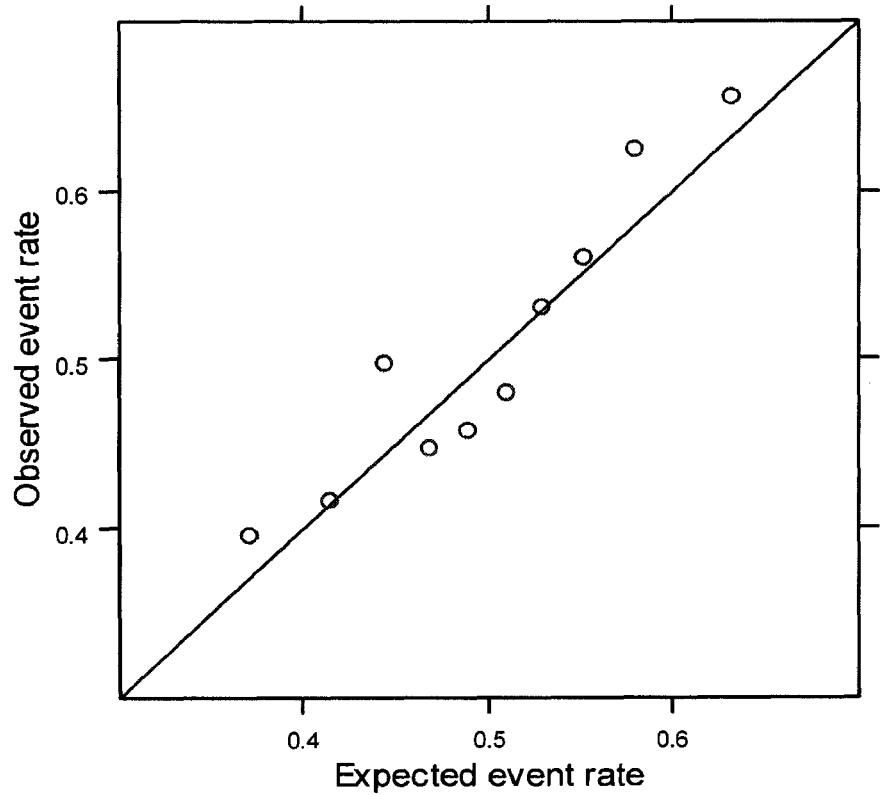
FIG. 1 depicts the results of a Hosmer-Lemeshow test to assess calibration of the 10-SNP risk scores.

Unless specifically defined otherwise, all technical and scientific terms used herein shall be taken to have the same meaning as commonly understood by one of ordinary skill in the art (e.g., in cell culture, breast cancer analysis, molecular genetics, immunology, immunohistochemistry, protein chemistry, and biochemistry).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

It is to be understood that this invention is not limited to particular embodiments, which can, of course, vary. It is also to be understood that the terminology used herein is for the purpose of describing particular embodiments only, and is not intended to be limiting. As used in this specification and the appended claims, terms in the singular and the singular forms "a," "an" and "the," for example, optionally include plural referents unless the content clearly dictates otherwise. Thus, for example, reference to "a probe" optionally includes a plurality of probe molecules; similarly, depending on the context, use of the term "a nucleic acid" optionally includes, as a practical matter, many copies of that nucleic acid molecule.

As used herein, "breast cancer phenotype" refers to a phenotype that displays a predisposition towards developing breast cancer in an individual. A phenotype that displays a predisposition for breast cancer, can, for example, show a higher likelihood that the cancer will develop in an individual with the phenotype than in members of a relevant general population under a given set of environmental conditions (diet, physical activity regime, geographic location, etc.).

As used herein, "biological sample" refers to any sample that can be from or derived a human patient, e.g., bodily fluids (blood, saliva, urine etc.), biopsy, tissue, and/or waste from the patient. Thus, tissue biopsies, stool, sputum, saliva, blood, lymph, tears, sweat, urine, vaginal secretions, or the like can easily be screened for SNPs, as can essentially any tissue of interest that contains the appropriate nucleic acids. These samples are typically taken, following informed consent, from a patient by standard medical laboratory methods. The sample may be in a form taken directly from the patient, or may be at least partially processed (purified) to remove at least some non-nucleic acid material.

A "polymorphism" is a locus that is variable; that is, within a population, the nucleotide sequence at a polymorphism has more than one version or allele. One example of a polymorphism is a "single nucleotide polymorphism", which is a polymorphism at a single nucleotide position in a genome (the nucleotide at the specified position varies between individuals or populations).

As used herein, the term "SNP" or "single nucleotide polymorphism" refers to a genetic variation between individuals; e.g., a single nitrogenous base position in the DNA of organisms that is variable. As used herein, "SNPs" is the plural of SNP. Of course, when one refers to DNA herein, such reference may include derivatives of the DNA such as amplicons, RNA transcripts thereof, etc.

The term "allele" refers to one of two or more different nucleotide sequences that occur or are encoded at a specific locus, or two or more different polypeptide sequences encoded by such a locus. For example, a first allele can occur on one chromosome, while a second allele occurs on a second homologous chromosome, e.g., as occurs for different chromosomes of a heterozygous individual, or between different homozygous or heterozygous individuals in a population. An allele "positively" correlates with a trait when it is linked to it and when presence of the allele is an indicator that the trait or trait form will occur in an individual comprising the allele. An allele "negatively" correlates with a trait when it is linked to it and when presence of the allele is an indicator that a trait or trait form will not occur in an individual comprising the allele.

A marker polymorphism or allele is "correlated" or "associated" with a specified phenotype (breast cancer susceptibility, etc.) when it can be statistically linked (positively or negatively) to the phenotype. Methods for determining whether a polymorphism or allele is statistically linked are known to those in the art. That is, the specified polymorphism occurs more commonly in a case population (e.g., breast cancer patients) than in a control population (e.g., individuals that do not have breast cancer). This correlation is often inferred as being causal in nature, but it need not be simple genetic linkage to (association with) a locus for a trait that underlies the phenotype is sufficient for correlation/association to occur.

The phrase "linkage disequilibrium" (LD) is used to describe the statistical correlation between two neighbouring polymorphic genotypes. Typically, LD refers to the correlation between the alleles of a random gamete at the two loci, assuming Hardy-Weinberg equilibrium (statistical independence) between gametes. LD is quantified with either Lewontin's parameter of association (D') or with Pearson correlation coefficient (r) (Devlin and Risch, 1995). Two loci with a LD value of 1 are said to be in complete LD. At the other extreme, two loci with a LD value of 0 are termed to be in linkage equilibrium. Linkage disequilibrium is calculated following the application of the expectation maximization algorithm (EM) for the estimation of haplotype frequencies (Slatkin and Excoffier, 1996). LD values according to the present invention for neighbouring genotypes/loci are selected above 0.1, preferably, above 0.2, more preferable above 0.5, more preferably, above 0.6, still more preferably, above 0.7, preferably, above 0.8, more preferably above 0.9, ideally about 1.0.

"Allele frequency" refers to the frequency (proportion or percentage) at which an allele is present at a locus within an individual, within a line or within a population of lines. For example, for an allele "A," diploid individuals of genotype "AA," "Aa," or "aa" have allele frequencies of 1.0, 0.5, or 0.0, respectively. One can estimate the allele frequency within a line or population (e.g., cases or controls) by averaging the allele frequencies of a sample of individuals from that line or population. Similarly, one can calculate the allele frequency within a population of lines by averaging the allele frequencies of lines that make up the population.

An individual is "homozygous" if the individual has only one type of allele at a given locus (e.g., a diploid individual has a copy of the same allele at a locus for each of two homologous chromosomes). An individual is "heterozygous" if more than one allele type is present at a given locus (e.g., a diploid individual with one copy each of two different alleles). The term "homogeneity" indicates that members of a group have the same genotype at one or more specific loci. In contrast, the term "heterogeneity" is used to indicate that individuals within the group differ in genotype at one or more specific loci.

A "locus" is a chromosomal position or region. For example, a polymorphic locus is a position or region where a polymorphic nucleic acid, trait determinant, gene or marker is located. In a further example, a "gene locus" is a specific chromosome location (region) in the genome of a species where a specific gene can be found.

A "marker," "molecular marker" or "marker nucleic acid" refers to a nucleotide sequence or encoded product thereof (e.g., a protein) used as a point of reference when identifying a locus or a linked locus. A marker can be derived from genomic nucleotide sequence or from expressed nucleotide sequences (e.g., from an RNA, nRNA, mRNA, a cDNA, etc.), or from an encoded polypeptide. The term also refers to nucleic acid sequences complementary to or flanking the marker sequences, such as nucleic acids used as probes or primer pairs capable of amplifying the marker sequence. A "marker probe" is a nucleic acid sequence or molecule that can be used to identify the presence of a marker locus, e.g., a nucleic acid probe that is complementary to a marker locus sequence. Nucleic acids are "complementary" when they specifically hybridize in solution, e.g., according to Watson-Crick base pairing rules. A "marker locus" is a locus that can be used to track the presence of a second linked locus, e.g., a linked or correlated locus that encodes or contributes to the population variation of a phenotypic trait. For example, a marker locus can be used to monitor segregation of alleles at a locus, such as a QTL, that are genetically or physically linked to the marker locus. Thus, a "marker allele," alternatively an "allele of a marker locus" is one of a plurality of polymorphic nucleotide sequences found at a marker locus in a population that is polymorphic for the marker locus. In one aspect, the present invention provides marker loci correlating with a phenotype of interest, e.g., breast cancer susceptibility/resistance. Each of the identified markers is expected to be in close physical and genetic proximity (resulting in physical and/or genetic linkage) to a genetic element, e.g., a QTL, that contributes to the relevant phenotype. Markers corresponding to genetic polymorphisms between members of a population can be detected by methods well-established in the art. These include, e.g., PCR-based sequence specific amplification methods, detection of restriction fragment length polymorphisms (RFLP), detection of isozyme markers, detection of allele specific hybridization (ASH), detection of single nucleotide extension, detection of amplified variable sequences of the genome, detection of self-sustained sequence replication, detection of simple sequence repeats (SSRs), detection of single nucleotide polymorphisms (SNPs), or detection of amplified fragment length polymorphisms (AFLPs).

The term "amplifying" in the context of nucleic acid amplification is any process whereby additional copies of a selected nucleic acid (or a transcribed form thereof) are produced. Typical amplification methods include various polymerase based replication methods, including the polymerase chain reaction (PCR), ligase mediated methods such as the ligase chain reaction (LCR) and RNA polymerase based amplification (e.g., by transcription) methods.

An "amplicon" is an amplified nucleic acid, e.g., a nucleic acid that is produced by amplifying a template nucleic acid by any available amplification method (e.g., PCR, LCR, transcription, or the like).

A specified nucleic acid is "derived from" a given nucleic acid when it is constructed using the given nucleic acid's sequence, or when the specified nucleic acid is constructed using the given nucleic acid.

A "gene" is one or more sequence(s) of nucleotides in a genome that together encode one or more expressed molecules, e.g., an RNA, or polypeptide. The gene can include coding sequences that are transcribed into RNA which may then be translated into a polypeptide sequence, and can include associated structural or regulatory sequences that aid in replication or expression of the gene.

A "genotype" is the genetic constitution of an individual (or group of individuals) at one or more genetic loci. Genotype is defined by the allele(s) of one or more known loci of the individual, typically, the compilation of alleles inherited from its parents.

A "haplotype" is the genotype of an individual at a plurality of genetic loci on a single DNA strand. Typically, the genetic loci described by a haplotype are physically and genetically linked, i.e., on the same chromosome strand.

A "set" of markers, probes or primers refers to a collection or group of markers probes, primers, or the data derived therefrom, used for a common purpose, e.g., identifying an individual with a specified genotype (e.g., risk of developing breast cancer). Frequently, data corresponding to the markers, probes or primers, or derived from their use, is stored in an electronic medium. While each of the members of a set possess utility with respect to the specified purpose, individual markers selected from the set as well as subsets including some, but not all of the markers, are also effective in achieving the specified purpose.

The polymorphisms and genes, and corresponding marker probes, amplicons or primers described above can be embodied in any system herein, either in the form of physical nucleic acids, or in the form of system instructions that include sequence information for the nucleic acids. For example, the system can include primers or amplicons corresponding to (or that amplify a portion of) a gene or polymorphism described herein. As in the methods above, the set of marker probes or primers optionally detects a plurality of polymorphisms in a plurality of said genes or genetic loci. Thus, for example, the set of marker probes or primers detects at least one polymorphism in each of these polymorphisms or genes, or any other polymorphism, gene or locus defined herein. Any such probe or primer can include a nucleotide sequence of any such polymorphism or gene, or a complementary nucleic acid thereof, or a transcribed product thereof (e.g., a nRNA or mRNA form produced from a genomic sequence, e.g., by transcription or splicing).

As used herein, "logistic regression" refers to methods for predicting the probability of occurrence of an event by fitting data to a logistic curve. One skilled in the art will understand how to employ such methods in the context of the invention.

As used herein, "Hosmer-Lemeshow test" refers to a statistical method for measuring the lack of fit of. Methods of using such are well-known in the art (Hosmer D W, Lemeshow S. Applied Logistic Regression. New York: Wiley; 1989: Section 5.2.2).

As used herein, "Receiver operating characteristic curves" refer to a graphical plot of the sensitivity vs. (1−specificity) for a binary classifier system as its discrimination threshold is varied. The ROC can also be represented equivalently by plotting the fraction of true positives (TPR=true positive rate) vs. the fraction of false positives (FPR=false positive rate). Also known as a Relative Operating Characteristic curve, because it is a comparison of two operating characteristics (TPR & FPR) as the criterion changes. ROC analysis provides tools to select possibly optimal models and to discard suboptimal ones independently from (and prior to specifying) the cost context or the class distribution. ROC analysis is related in a direct and natural way to cost/benefit analysis of diagnostic decision making. The ROC curve was first developed by electrical engineers and radar engineers during World War II for detecting enemy objects in battle fields, also known as the signal detection theory, and was soon introduced in psychology to account for perceptual detection of signals. ROC analysis since then has been used in medicine, radiology, and other areas for many decades, and it has been introduced relatively recently in other areas like machine learning and data mining. Methods of using in the context of the invention will be clear to those skilled in the art.

As used herein, the term "combining the clinical risk assessment with the genetic risk assessment to obtain the overall risk" refers to any suitable mathematical analysis relying on the results of the two assessments. For example, the results of the clinical risk assessment and the genetic risk assessment may be added, more preferably multiplied.

As used herein, the terms "routinely screening for breast cancer" and "more frequent screening" are relative terms, and are based on a comparison to the level of screening recommended to a subject who has no identified risk of developing breast cancer.

Clinical Risk Assessment

Any suitable clinical risk assessment procedure can be used in the present invention. Preferably, the clinical risk assessment does not involve genotyping the female at one or more loci. In an embodiment, the clinical risk assessment procedure includes obtaining information from the female on one or more of the following: medical history of breast cancer, ductal carcinoma or lobular carcinoma, age, menstrual history such as age of first menstrual period, age at which she first gave birth, family history of breast cancer or other cancer including the age of the relative at the time of diagnosis, results of previous breast biopsies, use of oral contraceptives, body mass index, alcohol consumption history, smoking history, exercise history, diet and race/ethnicity. Examples of clinical risk assessment procedures include, but are not limited to, the Gail Model (Gail et al., 1989, 1999 and 2007; Costantino et al., 1999; Rockhill et al., 2001), the Claus model (Claus et al., 1994 and 1998), Claus Tables, BOADICEA (Antoniou et al., 2002 and 2004), the Jonker Model (Jonker et al., 2003), the Claus Extended Formula (van Asperen et al., 2004), the Tyrer-Cuzick Model (Tyrer et al., 2004), the Manchester Scoring System (Evans et al., 2004), and the like. In a preferred embodiment, the clinical risk assessment procedure is the Gail Model.

The Gail Model is a statistical model which forms the basis of a breast cancer risk assessment tool, named after Dr. Mitchell Gail, Senior Investigator in the Biostatistics Branch of NCI's Division of Cancer Epidemiology and Genetics. The model uses a woman's own personal medical history (number of previous breast biopsies and the presence of atypical hyperplasia in any previous breast biopsy specimen), her own reproductive history (age at the start of menstruation and age at the first live birth of a child), and the history of breast cancer among her first-degree relatives (mother, sisters, daughters) to estimate her risk of developing invasive breast cancer over specific periods of time. Data from the Breast Cancer Detection Demonstration Project (BCDDP), which was a joint NCI and American Cancer Society breast cancer screening study that involved 280,000 women aged 35 to 74 years, and from NCI's Surveillance, Epidemiology, and End Results (SEER) Program were used in developing the model. Estimates for African American women were based on data from the Women's Contraceptive and Reproductive Experiences (CARE) Study and from SEER data. CARE participants included 1,607 women with invasive breast cancer and 1,637 without.

The Gail model has been tested in large populations of white women and has been shown to provide accurate estimates of breast cancer risk. In other words, the model has been "validated" for white women. It has also been tested in data from the Women's Health Initiative for African American women, and the model performs well, but may underestimate risk in African American women with previous biopsies. The model still needs to be validated for Hispanic women, Asian women, and other subgroups, and results should be interpreted by a health care provider for women with special risk factors, such as women treated for Hodgkin's disease with radiation to the chest and carriers of gene mutations that increase breast cancer risk. Researchers are conducting additional studies, including studies with minority populations, to gather more data and to test and improve the model.

Genetic Risk Assessment

The genetic risk assessment is performed by analysing the genotype of the subject at two or more loci for single nucleotide polymorphisms known to be associated with a breast cancer phenotype. As the skilled addressee will appreciate, each SNP has an odds ratio of association with breast cancer of greater than 1.0, more preferably greater than 1.02. Examples of such SNPs include, but are not limited to, those designated rs2981582, rs3803662, rs889312, rs13387042, rs13281615, rs4415084, rs3817198, rs4973768, rs6504950, rs11249433, rs10941679, rs2180341, rs3744448, rs16943468, rs1011970, rs2380205, rs10995190, rs704010 and rs614367 (see Table 1), or a single nucleotide polymorphism in linkage disequilibrium with one or more thereof.

TABLE 1

Examples of SNPs associated with a breast cancer phenotype.

| dbSNP rsID | Gene | Location | OR (95% CI)[2] | Reference |
|---|---|---|---|---|
| rs2981582 | FGFR2 | 10q | 1.26 (1.23-1.30) | Easton et al., 2007 |
| rs3803662 | TNRC9 | 16q | 1.20 (1.16-1.24) | Easton et al., 2007 |
| rs889312 | MAP3K1 | 5q | 1.13 (1.10-1.16) | Easton et al., 2007 |
| rs13387042 | (none) | 2q35 | 1.20 (1.14-1.26) | Stacey et al., 2007 |
| rs13281615 | (none) | 8q24 | 1.08 (1.05-1.11) | Easton et al., 2007 |
| rs4415084 | FGF10 | 5p | 1.16 (1.10-1.21) | Stacey et al., 2008 |
| rs3817198 | LSP1 | 11p | 1.07 (1.04-1.11) | Easton et al., 2007 |
| rs4973768 | SLC4A7 | 3p24 | 1.11 (1.08-1.13) | Ahmed et al., 2009 |
| rs6504950 | COX11 | 17q23.2 | 1.05 (1.03-1.09) | Ahmed et al., 2009 |
| rs11249433 | FCGR1B | 1p11.2 | 1.14 (1.10-1.19) | Thomas et al., 2009 |
| rs10941679 | | 5p12 | 1.19 | Stacey, et al 2008 |
| rs2180341 | ECHDC1 | 6q22 | 1.41 | Gold, et al 2008 |
| rs3744448 | TCF1 | 17q21 | 1.2 (1.00-1.50) | Keleman, et al 2009 |
| rs16943468 | YPEL2 | 17 | 1.30 (1.10-1.80) | Keleman, et al 2009 |
| rs1011970 | CDKN2A | 9p21 | 1.00 (0.89-1.12) | Turnbull, et al 2010 |
| rs2380205 | ANKRD16 | 10p15 | 1.14 (1.00-1.30) | Turnbull, et al 2010 |
| rs10995190 | ZNF365 | 10 | 1.01 (0.87-1.16) | Turnbull, et al 2010 |
| rs704010 | | 10q22 | 1.03 (0.90-1.17) | Turnbull, et al 2010 |
| rs614367 | | 11q13 | 1.17 (1.05-1.31) | Turnbull, et al 2010 |

In a preferred embodiment, the single nucleotide polymorphisms are selected from a group consisting of rs2981582, rs3803662, rs889312, rs13387042, rs13281615, rs4415084, and rs3817198, or a single nucleotide polymorphism in linkage disequilibrium with one or more thereof. In a further preferred embodiment, the single nucleotide polymorphisms are selected from a group consisting of rs2981582, rs3803662, rs889312, rs13387042, rs13281615, rs4415084, rs3817198, rs4973768, rs6504950 and rs11249433, or a single nucleotide polymorphism in linkage disequilibrium with one or more thereof.

The skilled person can readily identify SNPs in linkage disequilibrium with those specifically mentioned herein. Examples of such SNPs include rs1219648 and rs2420946 which are in strong linkage disequilibrium with rs2981582 (further possible examples provided in Table 2), rs12443621 and rs8051542 which are in strong linkage disequilibrium with SNP rs3803662 (further possible examples provided in Table 3), and rs10941679 which is in strong linkage disequilibrium with SNP rs4415084 (further possible examples provided in Table 4). In addition, examples of SNPs in linkage disequilibrium with rs13387042 provided in Table 5.

TABLE 2

Surrogate markers for SNP rs2981582. Markers with a r2 greater than 0.05 to rs2981582 in the HAPMAP dataset (http://hapmap.ncbi.nlm.nih.gov) in a 1 Mbp interval flanking the marker was selected. Shown is the name of the correlated SNP, values for r2 and D' to rs2981582 and the corresponding LOD value, as well as the position of the surrogate marker in NCB Build 36.

| DbSNP rsID | Position | Correlated SNP | Location | D' | $r^2$ | LOD |
|---|---|---|---|---|---|---|
| rs2981582 | 123342307 | rs3135715 | 123344716 | 1.000 | 0.368 | 15.02 |
| rs2981582 | 123342307 | rs7899765 | 123345678 | 1.000 | 0.053 | 2.44 |
| rs2981582 | 123342307 | rs1047111 | 123347551 | 0.938 | 0.226 | 9.11 |
| rs2981582 | 123342307 | rs1219639 | 123348302 | 1.000 | 0.143 | 6.53 |
| rs2981582 | 123342307 | rs10886955 | 123360344 | 0.908 | 0.131 | 5.42 |
| rs2981582 | 123342307 | rs1631281 | 123380775 | 0.906 | 0.124 | 5.33 |
| rs2981582 | 123342307 | rs3104685 | 123381354 | 0.896 | 0.108 | 4.58 |
| rs2981582 | 123342307 | rs1909670 | 123386718 | 1.000 | 0.135 | 6.12 |
| rs2981582 | 123342307 | rs7917459 | 123392364 | 1.000 | 0.135 | 6.42 |
| rs2981582 | 123342307 | rs17102382 | 123393846 | 1.000 | 0.135 | 6.42 |

TABLE 2-continued

Surrogate markers for SNP rs2981582. Markers with a r2 greater than 0.05 to rs2981582 in the HAPMAP dataset (http://hapmap.ncbi.nlm.nih.gov) in a 1 Mbp interval flanking the marker was selected. Shown is the name of the correlated SNP, values for r2 and D' to rs2981582 and the corresponding LOD value, as well as the position of the surrogate marker in NCB Build 36.

| DbSNP rsID | Position | Correlated SNP | Location | D' | r² | LOD |
|---|---|---|---|---|---|---|
| rs2981582 | 123342307 | rs10788196 | 123407625 | 1.000 | 0.202 | 9.18 |
| rs2981582 | 123342307 | rs2935717 | 123426236 | 0.926 | 0.165 | 7.30 |
| rs2981582 | 123342307 | rs3104688 | 123426455 | 0.820 | 0.051 | 2.07 |
| rs2981582 | 123342307 | rs4752578 | 123426514 | 1.000 | 0.106 | 5.15 |
| rs2981582 | 123342307 | rs1696803 | 123426940 | 0.926 | 0.168 | 7.33 |
| rs2981582 | 123342307 | rs12262574 | 123428112 | 1.000 | 0.143 | 7.39 |
| rs2981582 | 123342307 | rs4752579 | 123431182 | 1.000 | 0.106 | 5.15 |
| rs2981582 | 123342307 | rs12358208 | 123460953 | 0.761 | 0.077 | 2.46 |
| rs2981582 | 123342307 | rs17102484 | 123462020 | 0.758 | 0.065 | 2.39 |
| rs2981582 | 123342307 | rs2936859 | 123469277 | 0.260 | 0.052 | 1.56 |
| rs2981582 | 123342307 | rs10160140 | 123541979 | 0.590 | 0.016 | 0.40 |

TABLE 3

Surrogate markers for SNP rs3803662. Markers with a r2 greater than 0.05 to rs3803662 in the HAPMAP dataset (http://hapmap.ncbi.nlm.nih.gov) in a 1 Mbp interval flanking the marker was selected. Shown is the name of the correlated SNP, values for r2 and D' to rs3803662 and the corresponding LOD value, as well as the position of the surrogate marker in NCB Build 36.

| DbSNP rsID | Position | Correlated SNP | Location | D' | r² | LOD |
|---|---|---|---|---|---|---|
| rs3803662 | 51143842 | rs4784227 | 51156689 | 0.968 | 0.881 | 31.08 |
| rs3803662 | 51143842 | rs3112572 | 51157948 | 1.000 | 0.055 | 1.64 |
| rs3803662 | 51143842 | rs3104747 | 51159425 | 1.000 | 0.055 | 1.64 |
| rs3803662 | 51143842 | rs3104748 | 51159860 | 1.000 | 0.055 | 1.64 |
| rs3803662 | 51143842 | rs3104750 | 51159990 | 1.000 | 0.055 | 1.64 |
| rs3803662 | 51143842 | rs3104758 | 51166534 | 1.000 | 0.055 | 1.64 |
| rs3803662 | 51143842 | rs3104759 | 51167030 | 1.000 | 0.055 | 1.64 |
| rs3803662 | 51143842 | rs9708611 | 51170166 | 1.000 | 0.169 | 4.56 |
| rs3803662 | 51143842 | rs12935019 | 51170538 | 1.000 | 0.088 | 4.04 |
| rs3803662 | 51143842 | rs4784230 | 51175614 | 1.000 | 0.085 | 4.19 |
| rs3803662 | 51143842 | rs11645620 | 51176454 | 1.000 | 0.085 | 4.19 |
| rs3803662 | 51143842 | rs3112633 | 51178078 | 1.000 | 0.085 | 4.19 |
| rs3803662 | 51143842 | rs3104766 | 51182036 | 0.766 | 0.239 | 7.55 |
| rs3803662 | 51143842 | rs3104767 | 51182239 | 0.626 | 0.167 | 4.88 |
| rs3803662 | 51143842 | rs3112625 | 51183053 | 0.671 | 0.188 | 5.62 |
| rs3803662 | 51143842 | rs12920540 | 51183114 | 0.676 | 0.195 | 5.84 |
| rs3803662 | 51143842 | rs3104774 | 51187203 | 0.671 | 0.188 | 5.62 |
| rs3803662 | 51143842 | rs7203671 | 51187646 | 0.671 | 0.188 | 5.62 |
| rs3803662 | 51143842 | rs3112617 | 51189218 | 0.666 | 0.177 | 5.44 |
| rs3803662 | 51143842 | rs11075551 | 51189465 | 0.666 | 0.177 | 5.44 |
| rs3803662 | 51143842 | rs12929797 | 51190445 | 0.676 | 0.19 | 5.87 |
| rs3803662 | 51143842 | rs3104780 | 51191415 | 0.671 | 0.184 | 5.65 |
| rs3803662 | 51143842 | rs12922061 | 51192501 | 0.832 | 0.631 | 19.14 |
| rs3803662 | 51143842 | rs3112612 | 51192665 | 0.671 | 0.184 | 5.65 |
| rs3803662 | 51143842 | rs3104784 | 51193866 | 0.666 | 0.177 | 5.44 |
| rs3803662 | 51143842 | rs12597685 | 51195281 | 0.671 | 0.184 | 5.65 |
| rs3803662 | 51143842 | rs3104788 | 51196004 | 0.666 | 0.177 | 5.44 |
| rs3803662 | 51143842 | rs3104800 | 51203877 | 0.625 | 0.17 | 4.99 |
| rs3803662 | 51143842 | rs3112609 | 51206232 | 0.599 | 0.163 | 4.86 |
| rs3803662 | 51143842 | rs3112600 | 51214089 | 0.311 | 0.016 | 0.57 |
| rs3803662 | 51143842 | rs3104807 | 51215026 | 0.302 | 0.014 | 0.52 |
| rs3803662 | 51143842 | rs3112594 | 51229030 | 0.522 | 0.065 | 1.56 |
| rs3803662 | 51143842 | rs4288991 | 51230665 | 0.238 | 0.052 | 1.53 |
| rs3803662 | 51143842 | rs3104820 | 51233304 | 0.528 | 0.069 | 1.60 |
| rs3803662 | 51143842 | rs3104824 | 51236594 | 0.362 | 0.067 | 1.93 |
| rs3803662 | 51143842 | rs3104826 | 51237406 | 0.362 | 0.067 | 1.93 |
| rs3803662 | 51143842 | rs3112588 | 51238502 | 0.354 | 0.062 | 1.80 |

TABLE 4

Surrogate markers for SNP rs4415084. Markers with a r2 greater than 0.05 to rs4415084 in the HAPMAP dataset (http://hapmap.ncbi.nlm.nih.gov) in a 1 Mbp interval flanking the marker was selected. Shown is the name of the correlated SNP, values for r2 and D' to rs4415084 and the corresponding LOD value, as well as the position of the surrogate marker in NCB Build 36.

| DbSNP rsID | Position | Correlated SNP | Location | D' | $r^2$ | LOD |
|---|---|---|---|---|---|---|
| rs4415084 | 44698272 | rs12522626 | 44721455 | 1.000 | 1.0 | 47.37 |
| rs4415084 | 44698272 | rs4571480 | 44722945 | 1.000 | 0.976 | 40.54 |
| rs4415084 | 44698272 | rs6451770 | 44727152 | 1.000 | 0.978 | 44.88 |
| rs4415084 | 44698272 | rs920328 | 44734808 | 1.000 | 0.893 | 39.00 |
| rs4415084 | 44698272 | rs920329 | 44738264 | 1.000 | 1.0 | 47.37 |
| rs4415084 | 44698272 | rs2218081 | 44740897 | 1.000 | 1.0 | 47.37 |
| rs4415084 | 44698272 | rs16901937 | 44744898 | 1.000 | 0.978 | 45.06 |
| rs4415084 | 44698272 | rs11747159 | 44773467 | 0.948 | 0.747 | 28.79 |
| rs4415084 | 44698272 | rs2330572 | 44776746 | 0.952 | 0.845 | 34.31 |
| rs4415084 | 44698272 | rs994793 | 44779004 | 0.952 | 0.848 | 34.49 |
| rs4415084 | 44698272 | rs1438827 | 44787713 | 0.948 | 0.749 | 29.76 |
| rs4415084 | 44698272 | rs7712949 | 44806102 | 0.948 | 0.746 | 29.19 |
| rs4415084 | 44698272 | rs11746980 | 44813635 | 0.952 | 0.848 | 34.49 |
| rs4415084 | 44698272 | rs16901964 | 44819012 | 0.949 | 0.768 | 30.54 |
| rs4415084 | 44698272 | rs727305 | 44831799 | 0.972 | 0.746 | 27.65 |
| rs4415084 | 44698272 | rs10462081 | 44836422 | 0.948 | 0.749 | 29.76 |
| rs4415084 | 44698272 | rs13183209 | 44839506 | 0.925 | 0.746 | 28.55 |
| rs4415084 | 44698272 | rs13159598 | 44841683 | 0.952 | 0.848 | 34.19 |
| rs4415084 | 44698272 | rs3761650 | 44844113 | 0.947 | 0.744 | 28.68 |
| rs4415084 | 44698272 | rs13174122 | 44846497 | 0.971 | 0.735 | 26.70 |
| rs4415084 | 44698272 | rs11746506 | 44848323 | 0.973 | 0.764 | 29.24 |
| rs4415084 | 44698272 | rs7720787 | 44853066 | 0.952 | 0.845 | 34.31 |
| rs4415084 | 44698272 | rs9637783 | 44855403 | 0.948 | 0.748 | 29.16 |
| rs4415084 | 44698272 | rs4457089 | 44857493 | 0.948 | 0.762 | 29.70 |
| rs4415084 | 44698272 | rs6896350 | 44868328 | 0.948 | 0.764 | 29.46 |
| rs4415084 | 44698272 | rs1371025 | 44869990 | 0.973 | 0.785 | 30.69 |
| rs4415084 | 44698272 | rs4596389 | 44872313 | 0.948 | 0.749 | 29.76 |
| rs4415084 | 44698272 | rs6451775 | 44872545 | 0.948 | 0.746 | 29.19 |
| rs4415084 | 44698272 | rs729599 | 44878017 | 0.948 | 0.748 | 29.16 |
| rs4415084 | 44698272 | rs987394 | 44882135 | 0.948 | 0.749 | 29.76 |
| rs4415084 | 44698272 | rs4440370 | 44889109 | 0.948 | 0.748 | 29.16 |
| rs4415084 | 44698272 | rs7703497 | 44892785 | 0.948 | 0.749 | 29.76 |
| rs4415084 | 44698272 | rs13362132 | 44894017 | 0.952 | 0.827 | 34.09 |
| rs4415084 | 44698272 | rs1438821 | 44894208 | 0.951 | 0.844 | 34.52 |

TABLE 5

Surrogate markers for SNP rs13387042. Markers with a r2 greater than 0.05 to rs13387042 in the HAPMAP dataset (http://hapmap.ncbi.nlm.nih.gov) in a 1 Mbp interval flanking the marker was selected. Shown is the name of the correlated SNP, values for r2 and D' to rs13387042 and the corresponding LOD value, as well as the position of the surrogate marker in NCB Build 36.

| DbSNP rsID | Position | Correlated SNP | Location | D' | $r^2$ | LOD |
|---|---|---|---|---|---|---|
| rs13387042 | 217614077 | rs4621152 | 217617230 | 0.865 | 0.364 | 15.30 |
| rs13387042 | 217614077 | rs6721996 | 217617708 | 1.000 | 0.979 | 50.46 |
| rs13387042 | 217614077 | rs12694403 | 217623659 | 0.955 | 0.33 | 14.24 |
| rs13387042 | 217614077 | rs17778427 | 217631258 | 1.000 | 0.351 | 16.12 |
| rs13387042 | 217614077 | rs17835044 | 217631850 | 1.000 | 0.351 | 16.12 |
| rs13387042 | 217614077 | rs7588345 | 217632061 | 1.000 | 0.193 | 8.93 |
| rs13387042 | 217614077 | rs7562029 | 217632506 | 1.000 | 0.413 | 20.33 |
| rs13387042 | 217614077 | rs13000023 | 217632639 | 0.949 | 0.287 | 12.20 |
| rs13387042 | 217614077 | rs13409592 | 217634573 | 0.933 | 0.192 | 7.69 |
| rs13387042 | 217614077 | rs2372957 | 217635302 | 0.855 | 0.168 | 5.97 |
| rs13387042 | 217614077 | rs16856888 | 217638914 | 0.363 | 0.101 | 3.31 |
| rs13387042 | 217614077 | rs16856890 | 217639976 | 0.371 | 0.101 | 3.29 |
| rs13387042 | 217614077 | rs7598926 | 217640464 | 0.382 | 0.109 | 3.60 |
| rs13387042 | 217614077 | rs6734010 | 217643676 | 0.543 | 0.217 | 7.90 |
| rs13387042 | 217614077 | rs13022815 | 217644369 | 0.800 | 0.319 | 12.94 |
| rs13387042 | 217614077 | rs16856893 | 217645298 | 0.739 | 0.109 | 3.45 |
| rs13387042 | 217614077 | rs13011060 | 217646422 | 0.956 | 0.352 | 14.71 |
| rs13387042 | 217614077 | rs4674132 | 217646764 | 0.802 | 0.327 | 13.10 |
| rs13387042 | 217614077 | rs16825211 | 217647249 | 0.912 | 0.326 | 12.95 |
| rs13387042 | 217614077 | rs41521045 | 217647581 | 0.903 | 0.112 | 4.70 |
| rs13387042 | 217614077 | rs2372960 | 217650960 | 0.678 | 0.058 | 2.12 |

TABLE 5-continued

Surrogate markers for SNP rs13387042. Markers with a r2 greater than 0.05
to rs13387042 in the HAPMAP dataset (http://hapmap.ncbi.nlm.nih.gov) in a 1 Mbp
interval flanking the marker was selected. Shown is the name of the correlated SNP,
values for r2 and D' to rs13387042 and the corresponding LOD value, as well as the
position of the surrogate marker in NCB Build 36.

| DbSNP rsID | Position | Correlated SNP | Location | D' | r² | LOD |
|---|---|---|---|---|---|---|
| rs13387042 | 217614077 | rs2372967 | 217676158 | 0.326 | 0.052 | 1.97 |
| rs13387042 | 217614077 | rs3843337 | 217677680 | 0.326 | 0.052 | 1.97 |
| rs13387042 | 217614077 | rs2372972 | 217679386 | 0.375 | 0.062 | 2.28 |
| rs13387042 | 217614077 | rs9677455 | 217680497 | 0.375 | 0.062 | 2.28 |
| rs13387042 | 217614077 | rs12464728 | 217686802 | 0.478 | 0.073 | 2.54 |

In a preferred embodiment, the two or more SNPs at least include rs2981582, or a SNP in linkage disequilibrium therewith such as rs1219648 or rs2420946. More preferably, the two or more SNPs at least additionally include rs3803662 and rs889312, or SNPs in linkage disequilibrium therewith. Even more preferably, the two or more SNPs at least further additionally include rs13387042 and rs4415084, or SNPs in linkage disequilibrium therewith.

Marker Amplification Strategies

Amplification primers for amplifying markers (e.g., marker loci) and suitable probes to detect such markers or to genotype a sample with respect to multiple marker alleles, can be used in the invention. For example, primer selection for long-range PCR is described in U.S. Ser. No. 10/042,406 and U.S. Ser. No. 10/236,480; for short-range PCR, U.S. Ser. No. 10/341,832 provides guidance with respect to primer selection. Also, there are publicly available programs such as "Oligo" available for primer design. With such available primer selection and design software, the publicly available human genome sequence and the polymorphism locations, one of skill can construct primers to amplify the SNPs to practice the invention. Further, it will be appreciated that the precise probe to be used for detection of a nucleic acid comprising a SNP (e.g., an amplicon comprising the SNP) can vary, e.g., any probe that can identify the region of a marker amplicon to be detected can be used in conjunction with the present invention. Further, the configuration of the detection probes can, of course, vary. Thus, the invention is not limited to the sequences recited herein.

Indeed, it will be appreciated that amplification is not a requirement for marker detection, for example one can directly detect unamplified genomic DNA simply by performing a Southern blot on a sample of genomic DNA. Procedures for performing Southern blotting, standard amplification (PCR, LCR, or the like) and many other nucleic acid detection methods are well established and are taught, e.g., in Sambrook et al. (supra).

Separate detection probes can also be omitted in amplification/detection methods, e.g., by performing a real time amplification reaction that detects product formation by modification of the relevant amplification primer upon incorporation into a product, incorporation of labelled nucleotides into an amplicon, or by monitoring changes in molecular rotation properties of amplicons as compared to unamplified precursors (e.g., by fluorescence polarization).

Typically, molecular markers are detected by any established method available in the art, including, without limitation, allele specific hybridization (ASH), detection of single nucleotide extension, array hybridization (optionally including ASH), or other methods for detecting single nucleotide polymorphisms (SNPs), amplified fragment length polymorphism (AFLP) detection, amplified variable sequence detection, randomly amplified polymorphic DNA (RAPD) detection, restriction fragment length polymorphism (RFLP) detection, self-sustained sequence replication detection, simple sequence repeat (SSR) detection, single-strand conformation polymorphisms (SSCP) detection, isozyme marker detection, northern analysis (where expression levels are used as markers), quantitative amplification of mRNA or cDNA, or the like.

Examples of oligonucleotide primers useful for amplifying nucleic acids comprising SNPs known to be associated with a breast cancer phenotype are provided in Table 6. As the skilled person will appreciate, the sequence of the genomic region to which these oligonucleotides hybridize can be used to design primers which are longer at the 5' and/or 3' end, possibly shorter at the 5' and/or 3' (as long as the truncated version can still be used for amplification), which have one or a few nucleotide differences (but nonetheless can still be used for amplification), or which share no sequence similarity with those provided but which are designed based on genomic sequences close to where the specifically provided oligonucleotides hybridize and which can still be used for amplification.

Example Techniques for Marker Detection

Markers corresponding to genetic polymorphisms between members of a population can be detected by numerous methods well-established in the art (e.g., PCR-based sequence specific amplification, restriction fragment length polymorphisms (RFLPs), isozyme markers, northern analysis, allele specific hybridization (ASH), array based hybridization, amplified variable sequences of the genome, self-sustained sequence replication, simple sequence repeat (SSR), single nucleotide polymorphism (SNP), random amplified polymorphic DNA ("RAPD") or amplified fragment length polymorphisms (AFLP). In one additional embodiment, the presence or absence of a molecular marker is determined simply through nucleotide sequencing of the polymorphic marker region. Any of these methods are readily adapted to high throughput analysis.

TABLE 6

Examples of oligonucleotide primers useful for the invention.

| Name | Sequence |
|---|---|
| rs889312_for | TATGGGAAGGAGTCGTTGAG (SEQ ID NO: 1) |
| rs6504950_for | CTGAATCACTCCTTGCCAAC (SEQ ID NO: 2) |

TABLE 6-continued

Examples of oligonucleotide primers useful for the invention.

| Name | Sequence |
| --- | --- |
| rs4973768_for | CAAAATGATCTGACTACTCC (SEQ ID NO: 3) |
| rs4415084_for | TGACCAGTGCTGTATGTATC (SEQ ID NO: 4) |
| rs3817198_for | TCTCACCTGATACCAGATTC (SEQ ID NO: 5) |
| rs3803662_for | TCTCTCCTTAATGCCTCTAT (SEQ ID NO: 6) |
| rs2981582_for | ACTGCTGCGGGTTCCTAAAG (SEQ ID NO: 7) |
| rs13387042_for | GGAAGATTCGATTCAACAAGG (SEQ ID NO: 8) |
| rs13281615_for | GGTAACTATGAATCTCATC (SEQ ID NO: 9) |
| rs11249433_for | AAAAGCAGAGAAAGCAGGG (SEQ ID NO: 10) |
| rs889312_rev | AGATGATCTCTGAGATGCCC (SEQ ID NO: 11) |
| rs6504950_rev | CCAGGGTTTGTCTACCAAAG (SEQ ID NO: 12) |
| rs4973768_rev | AATCACTTAAAACAAGCAG (SEQ ID NO: 13) |
| rs4415084_rev | CACATACCTCTACCTCTAGC (SEQ ID NO: 14) |
| rs3817198_rev | TTCCCTAGTGGAGCAGTGG (SEQ ID NO: 15) |
| rs3803662_rev | CTTTCTTCGCAAATGGGTGG (SEQ ID NO: 16) |
| rs2981582_rev | GCACTCATCGCCACTTAATG (SEQ ID NO: 17) |
| rs13387042_rev | GAACAGCTAAACCAGAACAG (SEQ ID NO: 18) |
| rs13281615_rev | ATCACTCTTATTTCTCCCCC (SEQ ID NO: 19) |
| rs11249433_rev | TGAGTCACTGTGCTAAGGAG (SEQ ID NO: 20) |

Some techniques for detecting genetic markers utilize hybridization of a probe nucleic acid to nucleic acids corresponding to the genetic marker (e.g., amplified nucleic acids produced using genomic DNA as a template). Hybridization formats, including, but not limited to: solution phase, solid phase, mixed phase, or in situ hybridization assays are useful for allele detection. An extensive guide to the hybridization of nucleic acids is found in Tijssen (1993) Laboratory Techniques in Biochemistry and Molecular Biology—Hybridization with Nucleic Acid Probes Elsevier, New York, as well as in Sambrook et al. (supra).

For example, markers that comprise restriction fragment length polymorphisms (RFLP) are detected, e.g., by hybridizing a probe which is typically a sub-fragment (or a synthetic oligonucleotide corresponding to a sub-fragment) of the nucleic acid to be detected to restriction digested genomic DNA. The restriction enzyme is selected to provide restriction fragments of at least two alternative (or polymorphic) lengths in different individuals or populations. Determining one or more restriction enzyme that produces informative fragments for each allele of a marker is a simple procedure, well known in the art. After separation by length in an appropriate matrix (e.g., agarose or polyacrylamide) and transfer to a membrane (e.g., nitrocellulose, nylon, etc.), the labelled probe is hybridized under conditions which result in equilibrium binding of the probe to the target followed by removal of excess probe by washing.

Nucleic acid probes to the marker loci can be cloned and/or synthesized. Any suitable label can be used with a probe for use in the invention. Detectable labels suitable for use with nucleic acid probes include, for example, any composition detectable by spectroscopic, radioisotopic, photochemical, biochemical, immunochemical, electrical, optical or chemical means. Useful labels include biotin for staining with labelled streptavidin conjugate, magnetic beads, fluorescent dyes, radiolabels, enzymes, and calorimetric labels. Other labels include ligands which bind to antibodies labelled with fluorophores, chemiluminescent agents, and enzymes. A probe can also constitute radiolabelled PCR primers that are used to generate a radiolabelled amplicon. Labelling strategies for labelling nucleic acids and corresponding detection strategies can be found, e.g., in Haugland (2003) Handbook of Fluorescent Probes and Research Chemicals Ninth Edition by Molecular Probes, Inc. (Eugene Oreg.). Additional details regarding marker detection strategies are found below.

Amplification-Based Detection Methods

PCR, RT-PCR and LCR are in particularly broad use as amplification and amplification-detection methods for amplifying nucleic acids of interest (e.g., those comprising marker loci), facilitating detection of the nucleic acids of interest. Details regarding the use of these and other amplification methods can be found in any of a variety of standard texts, including, e.g., Sambrook et al. (supra). Many available biology texts also have extended discussions regarding PCR and related amplification methods. One of skill will appreciate that essentially any RNA can be converted into a double stranded DNA suitable for restriction digestion, PCR expansion and sequencing using reverse transcriptase and a polymerase ("Reverse Transcription-PCR, or "RT-PCR").

Real Time Amplification/Detection Methods

In one aspect, real time PCR or LCR is performed on the amplification mixtures described herein, e.g., using molecular beacons or TaqMan™ probes. A molecular beacon (MB) is an oligonucleotide or PNA which, under appropriate hybridization conditions, self-hybridizes to form a stem and loop structure. The MB has a label and a quencher at the termini of the oligonucleotide or PNA; thus, under conditions that permit intra-molecular hybridization, the label is typically quenched (or at least altered in its fluorescence) by the quencher. Under conditions where the MB does not display intra-molecular hybridization (e.g., when bound to a target nucleic acid, e.g., to a region of an amplicon during amplification), the MB label is unquenched. Details regarding standard methods of making and using MBs are well established in the literature and MBs are available from a number of commercial reagent sources (see also, e.g., Leone et al., 1995; Tyagi and Kramer, 1996; Blok and Kramer, 1997; Hsuih et al., 1997; Kostrikis et al., 1998; Sokol et al., 1998; Tyagi et al., 1998; Bonnet et al., 1999; Fang et al., 1999; Marras et al., 1999; and Vet et al., 1999). Additional details regarding MB construction and use is found in the patent literature, e.g., U.S. Pat. Nos. 5,925,517, 6,150,097 and 6,037,130.

PCR detection using dual-labelled fluorogenic oligonucleotide probes, commonly referred to as "TaqMan™" probes, can also be performed according to the present invention. These probes are composed of short (e.g., 20-25 base) oligodeoxynucleotides that are labelled with two different fluorescent dyes. On the 5' terminus of each probe is a reporter dye, and on the 3' terminus of each probe a quenching dye is found. The oligonucleotide probe sequence is complementary to an internal target sequence present in a PCR amplicon. When the probe is intact, energy transfer occurs between the two fluorophores and emission from the reporter is quenched by the quencher by FRET. During the extension phase of PCR, the probe is cleaved by 5' nuclease activity of the polymerase used in the reaction, thereby releasing the reporter from the oligonucleotide-quencher and producing an increase in reporter emission intensity. Accordingly, TaqMan™ probes are oligonucleotides that have a label and a quencher, where the label is released during amplification by the exonuclease action of the polymerase used in amplification. This provides a real time measure of amplification during synthesis. A variety of TaqMan™ reagents are commercially available, e.g., from Applied Biosystems (Division Headquarters in Foster City, Calif.) as well as from a variety of specialty vendors such as Biosearch Technologies (e.g., black hole quencher probes). Further details regarding dual-label probe strategies can be found, e.g., in WO 92/02638.

Other similar methods include e.g. fluorescence resonance energy transfer between two adjacently hybridized probes, e.g., using the "LightCycler®" format described in U.S. Pat. No. 6,174,670.

Array-Based Marker Detection

Array-based detection can be performed using commercially available arrays, e.g., from Affymetrix (Santa Clara, Calif.) or other manufacturers. Reviews regarding the operation of nucleic acid arrays include Sapolsky et al., 1999; Lockhart, 1998; Fodor, 1997a; Fodor, 1997b and Chee et al., 1996. Array based detection is one preferred method for identification markers of the invention in samples, due to the inherently high-throughput nature of array based detection.

A variety of probe arrays have been described in the literature and can be used in the context of the present invention for detection of markers that can be correlated to the phenotypes noted herein. For example, DNA probe array chips or larger DNA probe array wafers (from which individual chips would otherwise be obtained by breaking up the wafer) are used in one embodiment of the invention. DNA probe array wafers generally comprise glass wafers on which high density arrays of DNA probes (short segments of DNA) have been placed. Each of these wafers can hold, for example, approximately 60 million DNA probes that are used to recognize longer sample DNA sequences (e.g., from individuals or populations, e.g., that comprise markers of interest). The recognition of sample DNA by the set of DNA probes on the glass wafer takes place through DNA hybridization. When a DNA sample hybridizes with an array of DNA probes, the sample binds to those probes that are complementary to the sample DNA sequence. By evaluating to which probes the sample DNA for an individual hybridizes more strongly, it is possible to determine whether a known sequence of nucleic acid is present or not in the sample, thereby determining whether a marker found in the nucleic acid is present. One can also use this approach to perform ASH, by controlling the hybridization conditions to permit single nucleotide discrimination, e.g., for SNP identification and for genotyping a sample for one or more SNPs. Arrays provide one convenient embodiment for detecting multiple polymorphic markers simultaneously (or in series).

For example, breast cancer susceptibility detection arrays can be constructed in which any or all of the polymorphisms noted herein (or polymorphisms linked thereto) are detected simultaneously to assign a breast cancer susceptibility phenotype. Of course, any detection technology (PCR, LCR, real-time PCR, etc.) can similarly be used, e.g., with multiplex amplification/detection reactions, or simply by running several separate reactions, e.g., simultaneously or in series.

The use of DNA probe arrays to obtain allele information typically involves the following general steps: design and manufacture of DNA probe arrays, preparation of the sample, hybridization of sample DNA to the array, detection of hybridization events and data analysis to determine sequence. Preferred wafers are manufactured using a process adapted from semiconductor manufacturing to achieve cost effectiveness and high quality, and are available, e.g., from Affymetrix, Inc of Santa Clara, Calif.

For example, probe arrays can be manufactured by light-directed chemical synthesis processes, which combine solid-phase chemical synthesis with photolithographic fabrication techniques as employed in the semiconductor industry. Using a series of photolithographic masks to define chip exposure sites, followed by specific chemical synthesis steps, the process constructs high-density arrays of oligonucleotides, with each probe in a predefined position in the array. Multiple probe arrays can be synthesized simultaneously on a large glass wafer. This parallel process enhances reproducibility and helps achieve economies of scale.

Once fabricated, DNA probe arrays can be used to obtain data regarding presence and/or expression levels for markers of interest. The DNA samples may be tagged with biotin and/or a fluorescent reporter group by standard biochemical methods. The labelled samples are incubated with an array, and segments of the samples bind, or hybridize, with complementary sequences on the array. The array can be washed and/or stained to produce a hybridization pattern. The array is then scanned and the patterns of hybridization are detected by emission of light from the fluorescent reporter groups. Additional details regarding these procedures are found in the examples below. Because the identity and position of each probe on the array is known, the nature of the DNA sequences in the sample applied to the array can be determined. When these arrays are used for genotyping experiments, they can be referred to as genotyping arrays.

The nucleic acid sample to be analyzed is isolated, amplified and, typically, labelled with biotin and/or a fluorescent reporter group. The labelled nucleic acid sample is then incubated with the array using a fluidics station and hybridization oven. The array can be washed and or stained or counter-stained, as appropriate to the detection method. After hybridization, washing and staining, the array is inserted into a scanner, where patterns of hybridization are detected. The hybridization data are collected as light emitted from the fluorescent reporter groups already incorporated into the labelled nucleic acid, which is now bound to the probe array. Probes that most clearly match the labelled nucleic acid produce stronger signals than those that have mismatches. Since the sequence and position of each probe on the array are known, by complementarity, the identity of the nucleic acid sample applied to the probe array can be identified.

In one embodiment, two DNA samples may be differentially labelled and hybridized with a single set of the designed genotyping arrays. In this way two sets of data can be obtained from the same physical arrays. Labels that can be used include, but are not limited to, cychrome, fluorescein, or biotin (later stained with phycoerythrin-streptavidin after hybridization). Two-colour labelling is described in U.S. Pat. No. 6,342,355. Each array may be scanned such that the signal from both labels is detected simultaneously, or may be scanned twice to detect each signal separately.

Intensity data is collected by the scanner for all the markers for each of the individuals that are tested for presence of the marker. The measured intensities are a measure indicative of the amount of a particular marker present in the sample for a given individual (expression level and/or number of copies of the allele present in an individual, depending on whether genomic or expressed nucleic acids are analyzed). This can be used to determine whether the individual is homozygous or heterozygous for the marker of interest. The intensity data is processed to provide corresponding marker information for the various intensities.

Additional Details Regarding Nucleic Acid Amplification

As noted, nucleic acid amplification techniques such as PCR and LCR are well known in the art and can be applied to the present invention to amplify and/or detect nucleic acids of interest, such as nucleic acids comprising marker loci. Examples of techniques sufficient to direct persons of skill through such in vitro methods, including the polymerase chain reaction (PCR), the ligase chain reaction (LCR), Qβ-replicase amplification and other RNA polymerase mediated techniques (e.g., NASBA), are found in the references noted above, e.g., Sambrook et al. Additional details are found in U.S. Pat. No. 4,683,202; Kwoh et al., 1989; Guatelli et al., 1990; Landegren et al., 1988; Van Brunt, 1990; Wu and Wallace, 1989; Barringer et al., 1990; and Sooknanan and Malek, 1995. Improved methods of amplifying large nucleic acids by PCR, which is useful in the context of positional cloning of genes linked to the polymorphisms herein, are further summarized in Cheng et al. (1994), and the references therein, in which PCR amplicons of up to 40 kb are generated. Methods for long-range PCR are disclosed, for example, in U.S. Ser. No. 10/042,406; U.S. Ser. No. 10/236,480; and U.S. Pat. No. 6,740,510. U.S. Ser. No. 10/341,832 also provides details regarding primer picking methods for performing short range PCR.

Prior to amplification and/or detection of a nucleic acid comprising a marker, the nucleic acid is optionally purified from the samples by any available method, e.g., those taught in Berger and Kimmel, Guide to Molecular Cloning Techniques, Methods in Enzymology volume 152 Academic Press, Inc., San Diego, Calif., Sambrook et al. (supra), and/or Ausubel et al. (supra). A plethora of kits are also commercially available for the purification of nucleic acids from cells or other samples (see, e.g., EasyPrep™, FlexiPrep™, both from Pharmacia Biotech; StrataClean™, from Stratagene; and, QIAprep™ from Qiagen). Alternately, samples can simply be directly subjected to amplification or detection, e.g., following aliquotting and/or dilution.

Examples of markers can include polymorphisms, single nucleotide polymorphisms, presence of one or more nucleic acids in a sample, absence of one or more nucleic acids in a sample, presence of one or more genomic DNA sequences, absence or one or more genomic DNA sequences, presence of one or more mRNAs, absence of one or more mRNAs, expression levels of one or more mRNAs, presence of one or more proteins, expression levels of one or more proteins, and/or data derived from any of the preceding or combinations thereof. Essentially any number of markers can be detected, using available methods, e.g., using array technologies that provide high density, high throughput marker mapping. Thus, at least about 10, 100, 1,000, 10,000, or even 100,000 or more genetic markers can be tested, simultaneously or in a serial fashion (or combination thereof), for correlation to a relevant phenotype, in the first and/or second population. Combinations of markers can also be desirably tested, e.g., to identify genetic combinations or combinations of expression patterns in populations that are correlated to the phenotype.

Probe/Primer Synthesis Methods

In general, synthetic methods for making oligonucleotides, including probes, primers, molecular beacons, PNAs, LNAs (locked nucleic acids), etc., are well known. For example, oligonucleotides can be synthesized chemically according to the solid phase phosphoramidite triester method described by Beaucage and Caruthers (1981), e.g., using a commercially available automated synthesizer, e.g., as described in Needham-VanDevanter et al. (1984). Oligonucleotides, including modified oligonucleotides can also be ordered from a variety of commercial sources known to persons of skill. There are many commercial providers of oligo synthesis services, and thus this is a broadly accessible technology. Any nucleic acid can be custom ordered from any of a variety of commercial sources, such as The Midland Certified Reagent Company (mcrc@oligos.com), The Great American Gene Company (www.genco.com), ExpressGen Inc. (www.expressgen.com), Operon Technologies Inc. (Alameda, Calif.) and many others. Similarly, PNAs can be custom ordered from any of a variety of sources, such as PeptidoGenic (pkim@ccnet.com), HTI Bio-products, inc. (htibio.com), BMA Biomedicals Ltd (U.K.), Bio-Synthesis, Inc., and many others.

Amplification Primers for Marker Detection

In some preferred embodiments, the SNPs are detected using a suitable PCR-based detection method, where the size or sequence of the PCR amplicon is indicative of the absence or presence of the SNP. In these types of methods, PCR primers are hybridized to the conserved regions flanking the polymorphic region.

Suitable primers to be used with the invention can be designed using any suitable method. It is not intended that the invention be limited to any particular primer or primer pair. For example, primers can be designed using any suitable software program, such as LASERGENE®, e.g., taking account of publicly available sequence information. Flanking sequences for the polymorphisms identified herein are publicly available; accordingly, suitable amplification primers can be constructed based on well understood base-pairing rules. The sequence of any amplicon can be detected as has already been discussed above, e.g., by hybridization, array hybridization, PCR, real-time PCR, LCR, or the like.

In some embodiments, the primers of the invention are radiolabelled, or labelled by any suitable means (e.g., using a non-radioactive fluorescent tag), to allow for rapid visualization of differently sized amplicons following an amplification reaction without any additional labelling step or visualization step. In some embodiments, the primers are not labelled, and the amplicons are visualized following their size resolution, e.g., following agarose or acrylamide gel electrophoresis. In some embodiments, ethidium bromide staining of the PCR amplicons following size resolution allows visualization of the different size amplicons.

It is not intended that the primers of the invention be limited to generating an amplicon of any particular size. For example, the primers used to amplify the marker loci and alleles herein are not limited to amplifying the entire region of the relevant locus, or any subregion thereof. The primers can generate an amplicon of any suitable length for detection. In some embodiments, marker amplification produces an amplicon at least 20 nucleotides in length, or alternatively, at least 50 nucleotides in length, or alternatively, at least 100 nucleotides in length, or alternatively, at least 200 nucleotides in length. Amplicons of any size can be detected using the various technologies described herein. Differences in base composition or size can be detected by conventional methods such as electrophoresis.

Correlating Markers to Phenotypes

These correlations can be performed by any method that can identify a relationship between an allele and a phenotype, or a combination of alleles and a combination of phenotypes. For example, alleles in genes or loci defined herein can be correlated with one or more breast cancer phenotypes. Most typically, these methods involve referencing a look up table that comprises correlations between alleles of the polymorphism and the phenotype. The table can include data for multiple allele-phenotype relationships and can take account of additive or other higher order effects of multiple allele-phenotype relationships, e.g., through the use of statistical tools such as principle component analysis, heuristic algorithms, etc.

Correlation of a marker to a phenotype optionally includes performing one or more statistical tests for correlation. Many statistical tests are known, and most are computer-implemented for ease of analysis. A variety of statistical methods of determining associations/correlations between phenotypic traits and biological markers are known and can be applied to the present invention. Hartl (1981) A Primer of Population Genetics Washington University, Saint Louis Sinauer Associates, Inc. Sunderland, Mass. ISBN: 0-087893-271-2. A variety of appropriate statistical models are described in Lynch and Walsh (1998) Genetics and Analysis of Quantitative Traits, Sinauer Associates, Inc. Sunderland Mass. ISBN 0-87893-481-2. These models can, for example, provide for correlations between genotypic and phenotypic values, characterize the influence of a locus on a phenotype, sort out the relationship between environment and genotype, determine dominance or penetrance of genes, determine maternal and other epigenetic effects, determine principle components in an analysis (via principle component analysis, or "PCA"), and the like. The references cited in these texts provides considerable further detail on statistical models for correlating markers and phenotype.

In addition to standard statistical methods for determining correlation, other methods that determine correlations by pattern recognition and training, such as the use of genetic algorithms, can be used to determine correlations between markers and phenotypes. This is particularly useful when identifying higher order correlations between multiple alleles and multiple phenotypes. To illustrate, neural network approaches can be coupled to genetic algorithm-type programming for heuristic development of a structure-function data space model that determines correlations between genetic information and phenotypic outcomes. For example, NNUGA (Neural Network Using Genetic Algorithms) is an available program (e.g., on the world wide web at cs.bgu.ac.il/.about.omri/NNUGA which couples neural networks and genetic algorithms. An introduction to neural networks can be found, e.g., in Kevin Gurney, An Introduction to Neural Networks, UCL Press (1999) and on the world wide web at shef.ac.uk/psychology/gurney/notes/index.html. Additional useful neural network references include those noted above in regard to genetic algorithms and, e.g., Bishop, Neural Networks for Pattern Recognition, Oxford University Press (1995), and Ripley et al., Pattern Recognition and Neural Networks, Cambridge University Press (1995).

Additional references that are useful in understanding data analysis applications for using and establishing correlations, principle components of an analysis, neural network modelling and the like, include, e.g., Hinchliffe, Modelling Molecular Structures, John Wiley and Sons (1996), Gibas and Jambeck, Bioinformatics Computer Skills, O'Reilly (2001), Pevzner, Computational Molecular Biology and Algorithmic Approach, The MIT Press (2000), Durbin et al., Biological Sequence Analysis: Probabilistic Models of Proteins and Nucleic Acids, Cambridge University Press (1998), and Rashidi and Buehler, Bioinformatic Basics: Applications in Biological Science and Medicine, CRC Press LLC (2000).

In any case, essentially any statistical test can be applied in a computer implemented model, by standard programming methods, or using any of a variety of "off the shelf" software packages that perform such statistical analyses, including, for example, those noted above and those that are commercially available, e.g., from Partek Incorporated (St. Peters, Mo.; www.partek.com), e.g., that provide software for pattern recognition (e.g., which provide Partek Pro 2000 Pattern Recognition Software) which can be applied to genetic algorithms for multivariate data analysis, interactive visualization, variable selection, neural network & statistical modelling, etc. Relationships can be analyzed, e.g., by Principal Components Analysis (PCA) mapped scatterplots and biplots, Multi-Dimensional Scaling (MDS) Multi-Dimensional Scaling (MDS) mapped scatterplots, star plots, etc. Available software for performing correlation analysis includes SAS, R and MathLab.

The marker(s), whether polymorphisms or expression patterns, can be used for any of a variety of genetic analyses. For example, once markers have been identified, as in the present case, they can be used in a number of different assays for association studies. For example, probes can be designed for microarrays that interrogate these markers. Other exemplary assays include, e.g., the Taqman assays and molecular beacon assays described supra, as well as conventional PCR and/or sequencing techniques.

Additional details regarding association studies can be found in U.S. Ser. No. 10/106,097, U.S. Ser. No. 10/042,819, U.S. Ser. No. 10/286,417, U.S. Ser. No. 10/768,788, U.S. Ser. No. 10/447,685, U.S. Ser. No. 10/970,761, and U.S. Pat. No. 7,127,355.

In some embodiments, the marker data is used to perform association studies to show correlations between markers and phenotypes. This can be accomplished by determining marker characteristics in individuals with the phenotype of interest (i.e., individuals or populations displaying the phenotype of interest) and comparing the allele frequency or other characteristics (expression levels, etc.) of the markers in these individuals to the allele frequency or other characteristics in a control group of individuals. Such marker determinations can be conducted on a genome-wide basis, or can be focused on specific regions of the genome (e.g., haplotype blocks of interest). In one embodiment, markers that are linked to the genes or loci defined herein are assessed for correlation to one or more specific breast cancer susceptibility phenotypes.

In addition to the other embodiments of the methods of the present invention disclosed herein, the methods additionally allow for the "dissection" of a phenotype. That is, a particular phenotype can (and typically does) result from two or more different genetic bases. For example, a susceptibility phenotype in one individual may be the result of a "defect" (or simply a particular allele—"defect" with respect to a susceptibility phenotype is context dependent, e.g., whether the phenotype is desirable or undesirable in the individual in a given environment) in a gene defined in Table 1, while the same basic phenotype in a different individual may be the result of multiple "defects" in multiple genes. Thus, scanning a plurality of markers (e.g., as in genome or haplotype block scanning) allows for the dissection of varying genetic bases for similar (or graduated) phenotypes.

As described in the previous paragraph, one method of conducting association studies is to compare the allele frequency (or expression level) of markers in individuals with a phenotype of interest ("case group") to the allele frequency in a control group of individuals. In one method, informative SNPs are used to make the SNP haplotype pattern comparison (an "informative SNP" is genetic SNP marker such as a SNP or subset (more than one) of SNPs in a genome or haplotype block that tends to distinguish one SNP or genome or haplotype pattern from other SNPs, genomes or haplotype patterns). The approach of using informative SNPs has an advantage over other whole genome scanning or genotyping methods known in the art, for instead of reading all 3 billion bases of each individual's genome—or even reading the 3-4 million common SNPs that may be found—only informative SNPs from a sample population need to be detected. Reading these particular, informative SNPs provides sufficient information to allow statistically accurate association data to be extracted from specific experimental populations, as described above.

Thus, in an embodiment of one method of determining genetic associations, the allele frequency of informative SNPs is determined for genomes of a control population that do not display the phenotype. The allele frequency of informative SNPs is also determined for genomes of a population that do display the phenotype. The informative SNP allele frequencies are compared. Allele frequency comparisons can be made, for example, by determining the allele frequency (number of instances of a particular allele in a population divided by the total number of alleles) at each informative SNP location in each population and comparing these allele frequencies. The informative SNPs displaying a difference between the allele frequency of occurrence in the control versus case populations/groups are selected for analysis. Once informative SNPs are selected, the SNP haplotype block(s) that contain the informative SNPs are identified, which in turn identifies a genomic region of interest that is correlated with the phenotype. The genomic regions can be analyzed by genetic or any biological methods known in the art e.g., for use as drug discovery targets or as diagnostic markers.

Systems for performing the above correlations are also a feature of the invention. Typically, the system will include system instructions that correlate the presence or absence of an allele (whether detected directly or, e.g., through expression levels) with a predicted phenotype.

Optionally, the system instructions can also include software that accepts diagnostic information associated with any detected allele information, e.g., a diagnosis that a subject with the relevant allele has a particular phenotype. This software can be heuristic in nature, using such inputted associations to improve the accuracy of the look up tables and/or interpretation of the look up tables by the system. A variety of such approaches, including neural networks, Markov modelling, and other statistical analysis are described above.

The invention provides data acquisition modules for detecting one or more detectable genetic marker(s) (e.g., one or more arrays comprising one or more biomolecular probes, detectors, fluid handlers, or the like). The biomolecular probes of such a data acquisition module can include any that are appropriate for detecting the biological marker, e.g., oligonucleotide probes, proteins, aptamers, antibodies, etc. These can include sample handlers (e.g., fluid handlers), robotics, microfluidic systems, nucleic acid or protein purification modules, arrays (e.g., nucleic acid arrays), detectors, thermocyclers or combinations thereof, e.g., for acquiring samples, diluting or aliquoting samples, purifying marker materials (e.g., nucleic acids or proteins), amplifying marker nucleic acids, detecting amplified marker nucleic acids, and the like.

For example, automated devices that can be incorporated into the systems herein have been used to assess a variety of biological phenomena, including, e.g., expression levels of genes in response to selected stimuli (Service, 1998a), high throughput DNA genotyping (Zhang et al., 1999) and many others. Similarly, integrated systems for performing mixing experiments, DNA amplification, DNA sequencing and the like are also available (Service, 1998b). A variety of automated system components are available, e.g., from Caliper Technologies (Hopkinton, Mass.), which utilize various Zymate systems, which typically include, e.g., robotics and fluid handling modules. Similarly, the common ORCA® robot, which is used in a variety of laboratory systems, e.g., for microtiter tray manipulation, is also commercially available, e.g., from Beckman Coulter, Inc. (Fullerton, Calif.). Similarly, commercially available microfluidic systems that can be used as system components in the present invention include those from Agilent technologies and the Caliper Technologies. Furthermore, the patent and technical literature includes numerous examples of microfluidic systems, including those that can interface directly with microwell plates for automated fluid handling.

Any of a variety of liquid handling and/or array configurations can be used in the systems herein. One common format for use in the systems herein is a microtiter plate, in which the array or liquid handler includes a microtiter tray. Such trays are commercially available and can be ordered in a variety of well sizes and numbers of wells per tray, as well as with any of a variety of functionalized surfaces for binding of assay or array components. Common trays include the ubiquitous 96 well plate, with 384 and 1536 well plates also in common use. Samples can be processed in such trays, with all of the processing steps being performed in the trays. Samples can also be processed in microfluidic apparatus, or combinations of microtiter and microfluidic apparatus.

In addition to liquid phase arrays, components can be stored in or analyzed on solid phase arrays. These arrays fix materials in a spatially accessible pattern (e.g., a grid of rows and columns) onto a solid substrate such as a membrane (e.g., nylon or nitrocellulose), a polymer or ceramic surface, a glass or modified silica surface, a metal surface, or the like. Components can be accessed, e.g., by hybridization, by local rehydration (e.g., using a pipette or other fluid handling element) and fluidic transfer, or by scraping the array or cutting out sites of interest on the array.

The system can also include detection apparatus that is used to detect allele information, using any of the approached noted herein. For example, a detector configured to detect real-time PCR products (e.g., a light detector, such as a fluorescence detector) or an array reader can be incorporated into the system. For example, the detector can be configured to detect a light emission from a hybridization or amplification reaction comprising an allele of interest, wherein the light emission is indicative of the presence or absence of the allele. Optionally, an operable linkage between the detector and a computer that comprises the system instructions noted above is provided, allowing for automatic input of detected allele-specific information to the computer, which can, e.g., store the database information and/or execute the system instructions to compare the detected allele specific information to the look up table.

Probes that are used to generate information detected by the detector can also be incorporated within the system, along with any other hardware or software for using the probes to detect the amplicon. These can include thermocycler elements (e.g., for performing PCR or LCR amplification of the allele to be detected by the probes), arrays upon which the probes are arrayed and/or hybridized, or the like. The fluid handling elements noted above for processing samples, can be used for moving sample materials (e.g., template nucleic acids and/or proteins to be detected) primers, probes, amplicons, or the like into contact with one another. For example, the system can include a set of marker probes or primers configured to detect at least one allele of one or more genes or linked loci associated with a phenotype. The detector module is configured to detect one or more signal outputs from the set of marker probes or primers, or an amplicon produced from the set of marker probes or primers, thereby identifying the presence or absence of the allele.

The sample to be analyzed is optionally part of the system, or can be considered separate from it. The sample optionally includes e.g., genomic DNA, amplified genomic DNA, cDNA, amplified cDNA, RNA, amplified RNA, proteins, etc., as noted herein.

Optionally, system components for interfacing with a user are provided. For example, the systems can include a user viewable display for viewing an output of computer-implemented system instructions, user input devices (e.g., keyboards or pointing devices such as a mouse) for inputting user commands and activating the system, etc. Typically, the system of interest includes a computer, wherein the various computer-implemented system instructions are embodied in computer software, e.g., stored on computer readable media.

Standard desktop applications such as word processing software (e.g., Microsoft Word™ or Corel WordPerfect™) and database software (e.g., spreadsheet software such as Microsoft Excel™, Corel Quattro Pro™, or database programs such as Microsoft Access™ or Sequel™, Oracle™, Paradox™) can be adapted to the present invention by inputting a character string corresponding to an allele herein, or an association between an allele and a phenotype. For example, the systems can include software having the appropriate character string information, e.g., used in conjunction with a user interface (e.g., a GUI in a standard operating system such as a Windows, Macintosh or LINUX system) to manipulate strings of characters. Specialized sequence alignment programs such as BLAST can also be incorporated into the systems of the invention for alignment of nucleic acids or proteins (or corresponding character strings) e.g., for identifying and relating multiple alleles.

As noted, systems can include a computer with an appropriate database and an allele sequence or correlation of the invention. Software for aligning sequences, as well as data sets entered into the software system comprising any of the sequences herein can be a feature of the invention. The computer can be, e.g., a PC (Intel x86 or Pentium chip-compatible DOS™, OS2™ WINDOWS™ WINDOWS NT™, WINDOWS95™, WINDOWS98™, WINDOWS2000, WINDOWSME, or LINUX based machine, a MACINTOSH™, Power PC, or a UNIX based (e.g., SUN™ work station or LINUX based machine) or other commercially common computer which is known to one of skill. Software for entering and aligning or otherwise manipulating sequences is available, e.g., BLASTP and BLASTN, or can easily be constructed by one of skill using a standard programming language such as Visualbasic, Fortran, Basic, Java, or the like.

The invention provides methods of determining the polymorphic profile of an individual at one or more of SNPs of the invention. The SNPs includes those shown in Tables 1 to 5.

The polymorphic profile constitutes the polymorphic forms occupying the various polymorphic sites in an individual. In a diploid genome, two polymorphic forms, the same or different from each other, usually occupy each polymorphic site. Thus, the polymorphic profile at sites X and Y can be represented in the form X (x1, x1), and Y (y1, y2), wherein x1, x1 represents two copies of allele x1 occupying site X and y1, y2 represent heterozygous alleles occupying site Y.

The polymorphic profile of an individual can be scored by comparison with the polymorphic forms associated with resistance or susceptibility to breast cancer phenotypes occurring at each site. The comparison can be performed on at least, e.g., 1, 2, 5, 10, 25, 50, or all of the polymorphic sites, and optionally, others in linkage disequilibrium with them. The polymorphic sites can be analyzed in combination with other polymorphic sites. However, the total number of polymorphic sites analyzed is usually fewer than 10,000, 1000, 100, 50 or 25 and can be about 10 or less, about 5 or less, or about 2 or less.

The number of resistance or susceptibility alleles present in a particular individual can be combined additively or as ratio to provide an overall score for the individual's genetic propensity to breast cancer phenotypes (see U.S. 60/566,302, U.S. 60/590,534, U.S. Ser. No. 10/956,224, and WO/2005/086770). Resistance alleles can be arbitrarily each scored as +1 and susceptibility alleles as −1 (or vice versa). For example, if an individual is typed at 100 polymorphic sites of the invention and is homozygous for resistance at all of them, he could be assigned a score of 100% genetic propensity to resistance to breast cancer phenotypes or 0% propensity to susceptibility to breast cancer phenotypes. The reverse applies if the individual is homozygous for all susceptibility alleles. More typically, an individual is homozygous for resistance alleles at some loci, homozygous for susceptibility alleles at some loci, and heterozygous for resistance/susceptibility alleles at other loci. Such an individual's genetic propensity for breast cancer phenotypes can be scored by assigning all resistance alleles a score of +1, and all susceptibility alleles a score of −1 (or vice versa) and combining the scores. For example, if an individual has 102 resistance alleles and 204 susceptibility alleles, the individual can be scored as having a 33% genetic propensity to resistance and 67% genetic propensity to susceptibility. Alternatively, homozygous resistance alleles can be assigned a score of +1, heterozygous alleles a score of zero and homozygous susceptibility alleles a score of −1. The relative numbers of resistance alleles and susceptibility alleles can also be expressed as a percentage. Thus, an individual who is homozygous for resistance alleles at 30 polymorphic sites, homozygous for susceptibility alleles at 60 polymorphic sites, and heterozygous at the remaining 63 sites is assigned a genetic propensity of 33% for resistance.

As a further alternative, homozygosity for susceptibility can be scored as +2, heterozygosity, as +1 and homozygosity for resistance as 0.

The individual's score, and the nature of the polymorphic profile are useful in prognosis or diagnosis of an individual's susceptibility to a breast cancer phenotype. Optionally, a patient can be informed of susceptibility to a breast cancer phenotype indicated by the genetic profile. Presence of a high genetic propensity to breast cancer phenotypes can be treated as a warning to commence prophylactic or therapeutic treatment. For example, individuals with elevated risk of developing a breast cancer phenotype may be monitored differently (e.g., more frequent mammography) or may be treated prophylactically (e.g., with one or more drugs). Presence of a high propensity to a breast cancer phenotype also indicates the utility of performing secondary testing, such as a biopsy and other methods known in the art.

Polymorphic profiling is useful, for example, in selecting agents to affect treatment or prophylaxis of breast cancer phenotypes in a given individual. Individuals having similar polymorphic profiles are likely to respond to agents in a similar way.

Polymorphic profiling is also useful for stratifying individuals in clinical trials of agents being tested for capacity to treat breast cancer phenotypes or related conditions. Such trials are performed on treated or control populations having similar or identical polymorphic profiles (see EP 99965095.5), for example, a polymorphic profile indicating an individual has an increased risk of developing a breast cancer phenotype. Use of genetically matched populations eliminates or reduces variation in treatment outcome due to genetic factors, leading to a more accurate assessment of the efficacy of a potential drug. Computer-implemented algorithms can be used to identify more genetically homogenous subpopulations in which treatment or prophylaxis has a significant effect notwithstanding that the treatment or prophylaxis is ineffective in more heterogeneous larger populations. In such methods, data are provided for a first population with a breast cancer phenotype treated with an agent, and a second population also with the breast cancer phenotype but treated with a placebo. The polymorphic profile of individuals in the two populations is determined in at least one polymorphic site in or within 100 kb or 50 kb or 20 kb of a region defined by the SNPs provided in Tables 1 to 5. Data are also provided as to whether each patient in the populations reaches a desired endpoint indicative of successful treatment or prophylaxis. Subpopulations of each of the first and second populations are then selected such that the individuals in the subpopulations have greater similarity of polymorphic profiles with each other than do the individuals in the original first and second populations. There are many criteria by which similarity can be assessed. For example, one criterion is to require that individuals in the subpopulations have at least one susceptibility allele at each of at least one of the above genes. Another criterion is that individuals in the subpopulations have at least 75% susceptibility alleles for each of the polymorphic sites at which the polymorphic profile is determined. Regardless of the criteria used to assess similarity, the endpoint data of the subpopulations are compared to determine whether treatment or prophylaxis has achieved a statistically significant result in the subpopulations. As a result of computer implementation, billions of criteria for similarity can be analyzed to identify one or a few subpopulations showing statistical significance.

Polymorphic profiling is also useful for excluding individuals with no predisposition to breast cancer phenotypes from clinical trials. Including such individuals in the trial increases the size of the population needed to achieve a statistically significant result. Individuals with no predisposition to breast cancer phenotypes can be identified by determining the numbers of resistances and susceptibility alleles in a polymorphic profile as described above. For example, if a subject is genotyped at ten sites in ten genes of the invention associated with breast cancer phenotypes, twenty alleles are determined in total. If over 50% and preferably over 60% or 75% percent of these are resistance genes, the individual is unlikely to develop a breast cancer phenotype and can be excluded from the trial.

In other embodiments, stratifying individuals in clinical trials may be accomplished using polymorphic profiling in combination with other stratification methods, including, but not limited to, family history, risk models (e.g., Gail Score, Claus model), clinical phenotypes (e.g., atypical lesions), and specific candidate biomarkers.

Polymorphic profiles can also be used after the completion of a clinical trial to elucidated differences in response to a given treatment. For example, the set of polymorphisms can be used to stratify the enrolled patients into disease sub-types or classes. It is also possible to use the polymorphisms to identify subsets of patients with similar polymorphic profiles who have unusual (high or low) response to treatment or who do not respond at all (non-responders). In this way, information about the underlying genetic factors influencing response to treatment can be used in many aspects of the development of treatment (these range from the identification of new targets, through the design of new trials to product labelling and patient targeting). Additionally, the polymorphisms can be used to identify the genetic factors involved in adverse response to treatment (adverse events). For example, patients who show adverse response may have more similar polymorphic profiles than would be expected by chance. This allows the early identification and exclusion of such individuals from treatment. It also provides information that can be used to understand the biological causes of adverse events and to modify the treatment to avoid such outcomes.

Polymorphic profiles can also be used for other purposes, including paternity testing and forensic analysis as described by U.S. Pat. No. 6,525,185. In forensic analysis, the polymorphic profile from a sample at the scene of a crime is compared with that of a suspect. A match between the two is evidence that the suspect in fact committed the crime, whereas lack of a match excludes the suspect. The present polymorphic sites can be used in such methods, as can other polymorphic sites in the human genome.

EXAMPLES

Example 1—Evaluation of a SNP Panel for Breast Cancer Risk Assessment in a Nested Case-Control Study from the Women's Health Initiative Rationale The extent to which recently discovered breast cancer (BCa)-associated genetic variation can assist in BCa risk assessment is unclear. The effect of the addition of risk information from a panel of 7 BCa-associated SNPs on risk stratification offered by the Gail Model was assessed.

Methods 1664 women who developed BCa after randomization in the WHI Clinical Trial and 1636 matched BCa-free controls were examined. Controls were matched on the basis of baseline age, self-reported ethnicity, clinical trial participation, years since randomization, and hysterectomy status.

Seven SNPs from the published literature meeting rigorous criteria for genome-wide significance and replication were chosen to be genotyped (7-SNP Panel). To model SNP risk across the 7 selected panel SNPs, previously reported effect size estimates were used along with a multiplicative model for relative risk. To produce a combined clinical/genetic risk, Gail Model absolute risk estimates were multiplied by combined SNP relative risks to produce a combined clinical/genetic risk. Classification performance was assessed using reclassification tables to quantitate the net reclassification index (NRI), and receiver operating characteristic (ROC) curves.

Results

Individual SNP associations with BCa for white women were generally consistent with previous reports. Gail 5-year absolute risk and the 7-SNP relative risk estimate were both associated with BCa incidence when tested by logistic regression; there was a statistically significant (P=0.01), but very weak (r=0.044), correlation between Gail Risk and SNP Risk.

In this cohort, a two-fold increase in Gail risk yields a less-than two-fold increase in cancer incidence, suggesting that Gail risk is not so well calibrated in this dataset, which is consistent with a previous report (Chiebowski et al., 2007). The combined predictor was more strongly associated than either Gail risk or SNP components alone. In ROC curve analysis, the combination of Gail and SNP risk had an area under the curve (AUC) of 0.594 (95% CI: 0.576-0.612) compared to 0.556 (95% CI: 0.537-0.575) for Gail risk alone. The difference in AUC was statistically significant (95% CI: 0.025-0.050, empirical P<0.001). In the reclassification table analysis, 5-year risk thresholds that are potentially clinically meaningful in the context of decision-making about primary prevention were chosen: <1.5% (below average risk), 1.5-2% (moderate risk) and >2% (elevated risk). Reclassification in white women was evaluated for the combined SNPxGail Score versus Gail risk alone. The NRI in this context was 0.09 (Z=4.5, P=0.033) with improvement of classification for 6.4% of cases and 2.6% of controls.

Women with previous breast biopsies appear to be a subgroup with particular benefit from reclassification using the combined SNPxGail score.

In this subset, the Gail model had an AUC of 0.514 (95% CI: 0.471 to 0.561), indistinguishable from chance. Compared to the full cohort, the difference in AUC for the Gail model was borderline significant (95% CI: −0.002 to 0.081, empirical P=0.06). The combined model had an AUC of 0.571 (95% CI: 0.526 to 0.614). A bootstrap estimate of the difference in AUC for the combined model versus Gail alone was also significant (95% CI: 0.029 to 0.085, P<0.001).

Reclassification metrics in the biopsy subset indicated the NRI is 0.18, which is also very significant despite the smaller number of events (Z=3.9, P=4.9×10−5). Here, classification improved for 14.8% of controls (P=1.5×10−5) but only 2.8% of cases (P=0.16; Tables 7 and 8). Bootstrap resampling indicated that the difference in NRI between the full cohort and the biopsy subset was statistically significant. Based on 1000 bootstrap replicates, a 95% confidence interval for the improvement in NRI in the biopsy subset extended from 0.02 to 0.16, with empirical P=0.03.

TABLE 7

Logistic regression tests of association with breast cancer receptor subtypes.

| Predictor | ER-positive tumors | | ER-negative tumors | |
|---|---|---|---|---|
| | β (95% CI) | P | β (95% CI) | P |
| log(Gail 5-year risk) | 0.55 (0.37 to 0.72) | $1.1 \times 10^{-9}$ | −0.03 (−0.37 to 0.32) | 0.89 |
| log(SNP risk) | 1.20 (0.92 to 1.47) | $1.7 \times 10^{-18}$ | 0.56 (0.03 to 1.09) | 0.04 |
| log(SNP × Gail risk) | 0.72 (0.57 to 0.87) | $2.4 \times 10^{-22}$ | 0.14 (−0.14 to 0.43) | 0.32 |

TABLE 8

Combined odds ratio for the 7-SNP panel indicating improved predictive value for ER+ breast cancer as opposed to ER− breast cancer.

| dbSNP rsID | Gene | Risk Allele Freq | Odds Ratio of Breast Cancer | | |
|---|---|---|---|---|---|
| | | | All | ER+ | ER− |
| rs2981582 | FGFR2 | 0.38 | 1.26 | 1.3 | 1.035 |
| rs3803662 | TNRC9 | 0.25 | 1.2 | 1.275 | 1.105 |
| rs889312 | MAP3K1 | 0.28 | 1.13 | 1.12 | 1.07 |
| rs13387042 | (none) | 0.5 | 1.2 | 1.22 | 1.06 |
| rs13281615 | (none) | 0.4 | 1.08 | 1.13 | 1.03 |
| rs4415084 | FGF10 | 0.44 | 1.16 | 1.23 | 0.98 |
| rs3817198 | LSP1-H19 | 0.3 | 1.07 | 1.07 | 1.04 |
| Combined Odds Ratio | | | 2.7484 | 3.3682 | 1.2939 |

Discussion

A strategy combining both clinical risk factors (Gail risk) and well-validated common genetic risk factors (7-SNP panel) results in improvement in classification of BCa risks in white, postmenopausal women. This may have significant implications for informing primary prevention and/or screening strategies.

Example 2—Use of SNPs for Breast Cancer Risk Assessment: 10-SNP Model

SNP Genotyping

Ten (10) SNPs that have been reported to be associated with breast cancer with high statistical significance across multiple large sample sets were identified and are shown in Table 9.

Genotyping of 7 of the 10 SNPs is described in Example 1. The remaining 3 SNPs (rs4973768, rs6504950, rs11249433) were genotyped on the Sequenom MassArray platform. Two assays were designed in opposing orientations for each of the SNPs. Two of these SNPs (rs6504950 and rs11249433) had previously been genotyped on the same samples on oligonucleotide arrays. Samples that had performed poorly in previous Sequenom genotyping also performed poorly in this dataset, with agreement of less than 90% on these two SNPs, compared to 99.9% for the other samples. As a result, data for this same set of problematic samples was excluded.

Table 10 summarizes genotyping results for the 10 breast cancer associated SNPs.

TABLE 9

Replicated loci associated with invasive breast cancer.

| dbSNP rsID | Gene | Location | Freq[1] | OR (95% CI)[2] | Reference |
|---|---|---|---|---|---|
| rs2981582 | FGFR2 | 10q | 0.38 | 1.26 (1.23-1.30) | Easton et al., 2007 |
| rs3803662 | TNRC9 | 16q | 0.25 | 1.20 (1.16-1.24) | Easton et al., 2007 |
| rs889312 | MAP3K1 | 5q | 0.28 | 1.13 (1.10-1.16) | Easton et al., 2007 |
| rs13387042 | (none) | 2q35 | 0.50 | 1.20 (1.14-1.26) | Stacey et al., 2007 |
| rs13281615 | (none) | 8q24 | 0.40 | 1.08 (1.05-1.11) | Easton et al., 2007 |
| rs4415084 | FGF10 | 5p | 0.44 | 1.16 (1.10-1.21) | Stacey et al., 2008 |
| rs3817198 | LSP1 | 11p | 0.30 | 1.07 (1.04-1.11) | Easton et al., 2007 |
| rs4973768 | SLC4A7 | 3p24 | 0.46 | 1.11 (1.08-1.13) | Ahmed et al., 2009 |
| rs6504950 | COX11 | 17q23.2 | 0.73 | 1.05 (1.03-1.09) | Ahmed et al., 2009 |
| rs11249433 | FCGR1B | 1p11.2 | 0.39 | 1.14 (1.10-1.19) | Thomas et al., 2009 |

[1]Frequency of the high risk allele.
[2]Odds ratio (and confidence interval) per copy of the high risk allele.

TABLE 10

Genotyping performance of the breast cancer loci.

| dbSNP rsID | Platform | Call rate | Freq[1] | $P_{HWE}$[2] |
|---|---|---|---|---|
| rs2981582 | Array | 1.000 | 0.406 | 0.47 |
| rs3803662 | Array | 1.000 | 0.289 | 0.46 |
| rs889312 | Array | 0.996 | 0.285 | 0.68 |
| rs13387042 | Sequenom | 0.971 | 0.512 | 0.68 |
| rs13281615 | Array | 1.000 | 0.420 | 0.29 |
| rs4415084 | Array | 0.997 | 0.401 | 0.06 |
| rs3817198 | Array | 1.000 | 0.324 | 0.48 |
| rs4973768 | Sequenom | 0.997 | 0.496 | 0.14 |
| rs6504950 | Sequenom | 0.998 | 0.727 | 0.79 |
| rs11249433 | Sequenom | 0.995 | 0.426 | 0.82 |

[1]Frequency of the previously-reported high risk allele in white women.
[2]P value for Hardy-Weinberg equilibrium, from a likelihood ratio test, in white women.

Excluded were 264 samples from analyses that had more than 2 missing genotypes out of the 10 SNPs; for the remaining samples included in the analyses, 96% had complete data for the 10 SNPs.

Each SNP was individually tested for association with invasive breast cancer by logistic regression under a log additive model with no covariates. Results for white women were generally consistent with previous reports, as shown in Table 11.

TABLE 11

Single SNP tests of association with invasive breast cancer in white women.

| dbSNP rsID | OR (95% CI)[1] | P |
|---|---|---|
| rs2981582 | 1.37 (1.23-1.52) | $2.5 \times 10^{-9}$ |
| rs3803662 | 1.21 (1.08-1.35) | $1.0 \times 10^{-3}$ |
| rs889312 | 1.26 (1.13-1.41) | $4.9 \times 10^{-5}$ |
| rs13387042 | 1.16 (1.05-1.29) | 0.0032 |
| rs13281615 | 1.11 (1.00-1.23) | 0.042 |
| rs4415084 | 1.18 (1.06-1.31) | 0.0020 |
| rs3817198 | 1.12 (1.00-1.24) | 0.040 |
| rs4973768 | 1.03 (0.94-1.14) | 0.51 |
| rs6504950 | 1.08 (0.97-1.21) | 0.18 |
| rs11249433 | 1.10 (0.99-1.21) | 0.076 |

[1]Odds ratio (and confidence interval) per copy of the previously-reported high risk allele.

None of the new SNPs were significantly associated with breast cancer, but all of the tests trend in the expected direction and confidence intervals span the previously reported odds ratios. No significant pair-wise interactions among the 10 SNPs was detected (45 distinct tests yielded 2 tests with P<0.05, and none with P<0.01).

The Composite SNP Risk Score

To model SNP risk using the 10 selected breast cancer associated SNPs, estimates of effect sizes previously reported were used. A multiplicative model for relative risk across SNPs was used, where risk values for each SNP were scaled to have a population average of 1 based on the expected frequencies of the three possible diploid genotypes. Missing genotypes were also assigned a relative risk of 1.

Gail 5-year absolute risk and the 10-SNP relative risk estimate for association with breast cancer incidence by logistic regression with log-transformed risk estimates were separately tested. Both were strongly associated, as shown in Table 12.

TABLE 12

Logistic regression tests of association with invasive breast cancer in white women.

| Risk score | β (95% CI)[1] | OR per 2 × risk[2] | P |
|---|---|---|---|
| log(Gail 5-year risk) | 0.51 (0.34 to 0.68) | 1.42 (1.26-1.60) | $3.8 \times 10^{-9}$ |
| log(SNP risk) | 1.07 (0.83 to 1.30) | 2.09 (1.78-2.46) | $1.8 \times 10^{-19}$ |
| log(SNP × Gail risk) | 0.68 (0.54 to 0.82) | 1.61 (1.46-1.77) | $3.6 \times 10^{-23}$ |

[1]Logistic regression coefficient for the risk score.
[2]Fitted odds ratio corresponding to a 2-fold increase in the risk score.

Gail risk and SNP risk were weakly but significantly correlated (r=0.043, P=0.010). The combined predictor formed by multiplying the Gail absolute risk by the SNP relative risk was more strongly associated than either component alone. Including Gail risk and SNP risk as separate terms further improves the fit (P=1.8×10−4). An interaction term did not improve prediction of breast cancer status (P=0.50). The combined 10-SNP×Gail score appeared to be slightly more informative than the 7 SNP×Gail score: in a model with both scores, the 10-SNP×Gail score improved the fit over the 7-SNP score alone (likelihood ratio test: P=0.060) but not vice versa (P=0.47).

The Hosmer-Lemeshow test was used to assess calibration of the 10-SNP risk scores. As with the 7-SNP scores, the 10-SNP scores appear to be well calibrated (P=0.98, FIG. 1).

Classification Performance

Figure 2:
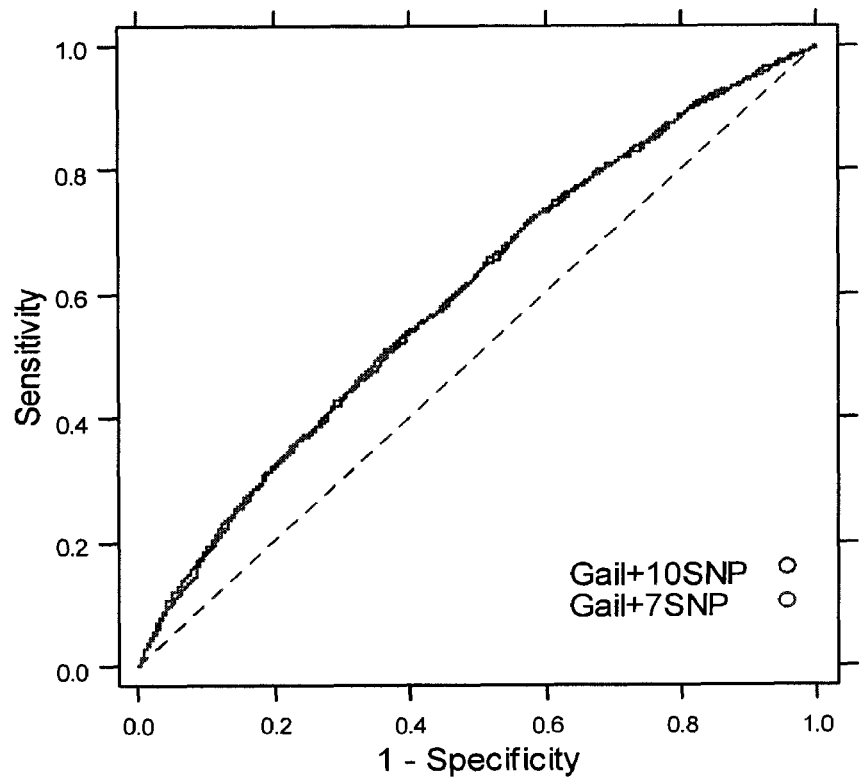
FIG. 2 depicts receiver operating characteristic curves for the combined 7-SNP and 10-SNP risk scores.

Classification performance was assessed using receiver operating characteristic (ROC) curves. AUC for the 7-SNP×Gail and 10-SNP×Gail scores is essentially unchanged (0.599 and 0.600, respectively), and the difference is not significant (FIG. 2).

Also evaluated was classification accuracy using reclassification tables (Cook et al., 2006), and quantified differences in classification by "net reclassification improvement" or NRI (Pencina et al., 2008). Five-year risk thresholds of 1.5% (for below-average risk) and 2% (for elevated risk) and evaluated reclassification for the combined SNP×Gail score versus Gail risk alone, in white women (Table 13).

TABLE 13

Reclassification table for SNP × Gail risk versus Gail risk in white women.

| Gail 5-year risk | SNP risk × Gail 5-year risk | | | |
|---|---|---|---|---|
| | <1.5% | 1.5%-2.0% | >2.0% | Total |
| <1.5% | | | | |
| Women | 942 | 245 | 86 | 1273 |
| Events | 400 | 131 | 57 | 588 |
| Nonevents | 542 | 114 | 29 | 685 |
| Proportion | 0.425 | 0.535 | 0.663 | 0.462 |
| 1.5%-2.0% | | | | |
| Women | 336 | 283 | 280 | 899 |
| Events | 147 | 139 | 169 | 455 |
| Nonevents | 189 | 145 | 111 | 445 |
| Proportion | 0.438 | 0.489 | 0.604 | 0.506 |
| >2.0% | | | | |
| Women | 49 | 134 | 724 | 907 |
| Events | 23 | 67 | 425 | 515 |
| Nonevents | 26 | 67 | 299 | 392 |
| Proportion | 0.469 | 0.500 | 0.587 | 0.568 |
| Total | | | | |
| Women | 1327 | 662 | 1090 | 3079 |
| Events | 570 | 337 | 651 | 1558 |
| Nonevents | 757 | 326 | 439 | 1522 |
| Proportion | 0.430 | 0.508 | 0.597 | 0.506 |

The NRI for this table is 0.095 ($Z=4.4$, $P=6.1\times10-6$). Classification improved for 7.7% of cases ($P=4.2\times10-7$), and 1.8% of controls ($P=0.11$). These results were slightly better than but not significantly different from results from the 7-SNP model.

Also directly evaluated was reclassification under the 10-SNP versus 7-SNP models. NRI for the 10-SNP model was 0.011, which was not significant ($Z=0.72$, $P=0.23$). Net reclassification of cases improved by 2.6% ($P=0.007$) but got worse for 1.6% of controls ($P=0.94$). If NRI is evaluated with a large number of threshold values, then the statistics improve because more women have changes in scores that are large enough to move them to a new category. For instance, with 25 thresholds at 4% quantiles of risk, NRI for the 10-SNP versus 7-SNP models is 0.056 ($Z=1.8$, $P=0.04$), and with 100 thresholds, NRI improves to 0.069 ($Z=2.0$, $P=0.02$).

Conclusions

In this dataset, it is demonstrated that the 10-SNP classifier is essentially as predictive and well calibrated as demonstrated for the 7-SNP classifier. The WHI dataset does not appear to be large enough to effectively demonstrate that the 10-SNP classifier is better than the 7-SNP classifier. However, the small improvement expected from adding SNPs to the model will likely be clinically meaningful in some contexts.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

All publications discussed and/or referenced herein are incorporated herein in their entirety.

The present application claims priority from U.S. 61/182,809 filed 1 Jun. 2009, and U.S. 61/258,420 filed 5 Nov. 2009, the entire contents of both of which are incorporated herein by reference.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Ahmed et al. (2009) Nature Genetics 41:585-590.
Antoniou et al. (2009) Hum Mol Genet 18:4442-4456.
Barringer et al. (1990) Gene 89:117-122.
Beaucage and Caruthers (1981) Tetrahedron Letts. 22:1859-1862.
Blok and Kramer (1997) Mol Cell Probes 11:187-194.
Bonnet et al. (1999) PNAS 96:6171-6176.
Chee et al. (1996) Science 274:610-614.
Cheng et al. (1994) Nature 369:684-685.
Chiebowski et al. (2007) J Natl Cancer Inst 99:1695-1705.
Cook et al. (2006) Ann Intern Med 145:21-29.
Costantino et al. (1999) J Natl Cancer Inst 91:1541-1548.
Devlin and Risch (1995) Genomics. 29: 311-322.
Easton et al. (2007) Nature 447: 1087-1093.
Fang et al. (1999) J. Am. Chem. Soc. 121:2921-2922.
Fodor (1997a) FASEB Journal 11:A879.
Fodor (1997b) Science 277: 393-395.
Gail et al. (1989) J Natl Cancer Inst 81:1879-1886.
Gail et al. (1999) J Natl Cancer Inst 91:1829-1846.
Gail et al. (2007) J Natl Cancer Inst 99(23):1782-1792.
Gold et al. (2008) PNAS 105: 4340-4345.
Guatelli et al. (1990) PNAS 87:1874-1878.
Hsuih et al. (1997) J Clin Microbiol 34:501-507.
Kelemen et al. (2009) Cancer Epidemiol Biomarkers Prev 18:1864-1868.
Kostrikis et al. (1998) Science 279:1228-1229.
Kwoh et al. (1989) PNAS 86:1173-1177.
Landegren et al. (1988) Science 241:1077-1080.
Leone et al. (1995) Nucleic Acids Res. 26:2150-2155.
Lockhart (1998) Nature Medicine 4:1235-1236.
Marras et al. (1999) Genet. Anal. Biomol. Eng. 14:151-156.
Needham Van Devanter et al. (1984) Nucleic Acids Res. 12:6159-6168.
Pencina et al. (2008) Stat Med 27:157-172.
Peto and Mako (2000) Nat Genet 26:411-414.
Rockhill et al. (2001) J Natl Cancer Inst 93(5):358-366.
Sapolsky et al. (1999) Genet Anal: Biomolec Engin 14:187-192.
Service (1998a) Science 282:396-399.
Service (1998b) Science 282: 399-401.
Slatkin and Excoffier (1996) Heredity 76: 377-383.
Sokol et al. (1998) PNAS 95:11538-11543.
Sooknanan and Malek (1995) Biotechnology 13: 563-564.
Stacey et al. (2007) Nature Genetics 39:965-869.

Stacey et al. (2008) Nature Genetics 40:703-706.
Thomas et al. (2009) Nature Genetics 41:579-584.
Turnbull et al. (2010) Nature Genetics 42: 504-509.
Tyagi and Kramer (1996) Nature Biotechnology 14:303-308.
Tyagi et al. (1998) Nature Biotechnology 16:49-53.
Van Brunt (1990) Biotechnology 8:291-294.
Vet et al. (1999) PNAS 96:6394-6399.
Wu and Wallace (1989) Gene 4:560-569.
Zhang et al. (1999) Anal. Chem. 71:1138-1145.

The invention claimed is:

1. A method for treating a human self-reported negroid female subject assessed to have a greater than 1.5% five-year risk of developing estrogen receptor-positive (ER-positive) breast cancer, comprising:
   i) identifying, by analysis of a biological sample from a human self-reported negroid female subject using probes or primers, the diploid genotypes at fewer than 100 polymorphic sites of the human self-reported negroid female subject including at each of single nucleotide polymorphisms (SNPs) rs2981582, rs3803662, rs889312, rs13387042, rs13281615, rs4415084, and rs3817198, thereby identifying the presence of zero, one, or two risk alleles at each of the SNPs, where an A or T at SNP rs2981582, a T or A at SNP rs3803662, a C or G at SNP rs889312, an A or T at SNP rs13387042, a C or G at SNP rs13281615, a T or A at SNP rs4415084, and a C or G at SNP rs3817198 are the risk allele,
   ii) obtaining a previously reported odds ratio of association with ER-positive breast cancer of each allele present at each of the SNPs determined in step i), which odds ratio of association with ER-positive breast cancer of each allele at each SNP has been scaled to have a population average at the SNP of 1 among human self-reported negroid females of the three possible diploid genotypes at that SNP,
   iii) multiplying together the odds ratio of association with ER-positive breast cancer of each allele present at each of the SNPs obtained in step ii),
   iv) producing the score of the human self-reported negroid female subject's risk of developing ER-positive breast cancer,
   v) selecting the human self-reported negroid female subject assessed to have a greater than 1.5% five-year risk of developing estrogen receptor-positive (ER-positive) breast cancer based on the score produced in step (iv), and
   vi) administering tamoxifen to the human self-reported negroid female subject assessed to have a greater than 1.5% five-year risk of developing estrogen receptor-positive (ER-positive) breast cancer.

2. The method of claim 1, wherein the human self-reported negroid female subject has used an oral contraceptive.

3. The method of claim 1, wherein the human self-reported negroid female subject has previously been treated for Hodgkin's disease with radiation to the chest.

4. The method of claim 1, wherein the human self-reported negroid female subject has a first-degree relative diagnosed with breast cancer, a mother diagnosed with breast cancer, a sister diagnosed with breast cancer, or a daughter diagnosed with breast cancer.

5. The method of claim 1, wherein the human self-reported negroid female subject is aged 35 to 74 years.

6. The method of claim 1, wherein the human self-reported negroid female subject is postmenopausal.

7. The method of claim 1, wherein the human self-reported negroid female subject has previously had a breast biopsy.

8. The method of claim 1, wherein the analysis of the biological sample from the human self-reported negroid female subject using probes or primers comprises nucleotide sequencing.

9. The method of claim 1, further comprising in step i) identifying the diploid genotypes of the human self-reported negroid female subject at each of SNPs rs4973768, rs6504950, and rs11249433, where a T or A at SNP rs4973768, a G or C at SNP rs6504950, and a G or C at SNP rs11249433 are the risk allele.

10. A method for treating a human self-reported negroid female subject assessed to have a greater than 1.5% five-year risk of developing estrogen receptor-positive (ER-positive) breast cancer, comprising:
   i) identifying, by analysis of a biological sample from a human self-reported negroid female subject using probes or primers, the diploid genotypes at fewer than 100 polymorphic sites of the human self-reported negroid female subject including at each of single nucleotide polymorphisms (SNPs) rs2981582, rs3803662, rs889312, rs13387042, rs13281615, rs4415084, and rs3817198, thereby identifying the presence of zero, one, or two risk alleles at each of the SNPs, where an A or T at SNP rs2981582, a T or A at SNP rs3803662, a C or G at SNP rs889312, an A or T at SNP rs13387042, a C or G at SNP rs13281615, a T or A at SNP rs4415084, and a C or G at SNP rs3817198 are the risk allele,
   ii) obtaining a previously reported odds ratio of association with ER-positive breast cancer of each allele present at each of the SNPs determined in step i), which odds ratio of association with ER-positive breast cancer of each allele at each SNP has been scaled to have a population average at the SNP of 1 among human self-reported negroid females of the three possible diploid genotypes at that SNP,
   iii) multiplying together the odds ratio of association with ER-positive breast cancer of each allele present at each of the SNPs obtained in step ii),
   iv) producing the score of the human self-reported negroid female subject's risk of developing ER-positive breast cancer,
   v) selecting the human self-reported negroid female subject assessed to have a greater than 1.5% five-year risk of developing estrogen receptor-positive (ER-positive) breast cancer based on the score produced in step iv), and vi) administering raloxifene to the human self-reported negroid female subject assessed to have a greater than 1.5% five-year risk of developing estrogen receptor-positive (ER-positive) breast cancer.

11. The method of claim 10, wherein the human self-reported negroid female subject has used an oral contraceptive.

12. The method of claim 10, wherein the human self-reported negroid female subject has previously been treated for Hodgkin's disease with radiation to the chest.

13. The method of claim 10, wherein the human self-reported negroid female subject has a first-degree relative diagnosed with breast cancer, a mother diagnosed with breast cancer, a sister diagnosed with breast cancer, or a daughter diagnosed with breast cancer.

14. The method of claim 10, wherein the human self-reported negroid female subject is aged 35 to 74 years.

15. The method of claim 10, wherein the human self-reported negroid female subject is postmenopausal.

16. The method of claim 10, wherein the human self-reported negroid female subject has previously had a breast biopsy.

17. The method of claim 10, wherein the analysis of the biological sample from the human self-reported negroid female subject using probes or primers comprises nucleotide sequencing.

18. The method of claim 10, further comprising in step i) identifying the diploid genotypes of the human self-reported negroid female subject at each of SNPs rs4973768, rs6504950, and rs11249433, where a T or A at SNP rs4973768, a G or C at SNP rs6504950, and a G or C at SNP rs11249433 are the risk allele.

19. A method for treating a human self-reported negroid female subject assessed to have a greater than 1.5% five-year risk of developing estrogen receptor-positive (ER-positive) breast cancer, comprising:
   i) identifying, by analysis of a biological sample from a human self-reported negroid female subject using probes or primers, the diploid genotypes at fewer than 100 polymorphic sites of the human self-reported negroid female subject including at each of single nucleotide polymorphisms (SNPs) rs2981582, rs3803662, rs889312, rs13387042, rs13281615, rs4415084, and rs3817198, thereby identifying the presence of zero, one, or two risk alleles at each of the SNPs, where an A or T at SNP rs2981582, a T or A at SNP rs3803662, a C or G at SNP rs889312, an A or T at SNP rs13387042, a C or G at SNP rs13281615, a T or A at SNP rs4415084, and a C or G at SNP rs3817198 are the risk allele,
   ii) obtaining a previously reported odds ratio of association with ER-positive breast cancer of each allele present at each of the SNPs determined in step i), which odds ratio of association with ER-positive breast cancer of each allele at each SNP has been scaled to have a population average at the SNP of 1 among human self-reported negroid females of the three possible diploid genotypes at that SNP,
   iii) multiplying together the odds ratio of association with ER-positive breast cancer of each allele present at each of the SNPs obtained in step ii),
   iv) producing the score of the human self-reported negroid female subject's risk of developing ER-positive breast cancer,
   v) selecting the human self-reported negroid female subject assessed to have a greater than 1.5% five-year risk of developing estrogen receptor-positive (ER-positive) breast cancer based on the score produced in step iv), and
   vi) administering an anti-breast cancer therapy that inhibits estrogen to the human self-reported negroid female subject assessed to have a greater than 1.5% five-year risk of developing estrogen receptor-positive (ER-positive) breast cancer.

20. The method of claim 19, further comprising in step i) identifying the diploid genotypes of the human self-reported negroid female subject at each of SNPs rs4973768, rs6504950, and rs11249433, where a T or A at SNP rs4973768, a G or C at SNP rs6504950, and a G or C at SNP rs11249433 are the risk allele.

* * * * *

```
                         SEQUENCE LISTING

<160> NUMBER OF SEQ ID NOS: 20

<210> SEQ ID NO 1
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 1
tatgggaagg agtcgttgag                                            20

<210> SEQ ID NO 2
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 2
ctgaatcact ccttgccaac                                            20

<210> SEQ ID NO 3
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 3
caaaatgatc tgactactcc                                            20

<210> SEQ ID NO 4
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 4
tgaccagtgc tgtatgtatc                                            20

<210> SEQ ID NO 5
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 5
tctcacctga taccagattc                                            20

<210> SEQ ID NO 6
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 6
```
tctctcctta atgcctctat                                           20

<210> SEQ ID NO 7
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 7
actgctgcgg gttcctaaag                                           20

<210> SEQ ID NO 8
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 8
ggaagattcg attcaacaag g                                         21

<210> SEQ ID NO 9
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 9
ggtaactatg aatctcatc                                            19

<210> SEQ ID NO 10
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 10
aaaaagcaga gaaagcaggg                                           20

<210> SEQ ID NO 11
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 11
agatgatctc tgagatgccc                                           20

<210> SEQ ID NO 12
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 12
ccagggtttg tctaccaaag                                           20

<210> SEQ ID NO 13
<211> LENGTH: 19
<212> TYPE: DNA
<213> ORGANISM: Artificial Sequence

```
<220> FEATURE:
<223> OTHER INFORMATION: Oligonucleotide primer

<400> SEQUENCE: 13
aatcacttaa aacaagcag                                                19

<210> SEQ ID NO 14
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 14
cacatacctc tacctctagc                                               20

<210> SEQ ID NO 15
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 15
ttccctagtg gagcagtgg                                                19

<210> SEQ ID NO 16
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 16
ctttcttcgc aaatgggtgg                                               20

<210> SEQ ID NO 17
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 17
gcactcatcg ccacttaatg                                               20

<210> SEQ ID NO 18
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 18
gaacagctaa accagaacag                                               20

<210> SEQ ID NO 19
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 19
atcactctta tttctccccc                                               20
```

```
<210> SEQ ID NO 20
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 20
tgagtcactg tgctaaggag                                            20
```